United States Patent
Clancy et al.

(10) Patent No.: US 7,226,587 B2
(45) Date of Patent: Jun. 5, 2007

(54) COMPOSITIONS AND METHODS FOR SYSTEMIC ADMINISTRATION OF SEQUENCES ENCODING BONE MORPHOGENETIC PROTEINS

(75) Inventors: Brian Clancy, Ashland, MA (US); Debra Pittman, Windham, NH (US); Howard Seeherman, Cambridge, MA (US)

(73) Assignee: Wyeth, Madison, NJ (US)

( * ) Notice: Subject to any disclaimer, the term of this patent is extended or adjusted under 35 U.S.C. 154(b) by 0 days.

(21) Appl. No.: 10/157,839

(22) Filed: May 31, 2002

(65) Prior Publication Data

US 2003/0170208 A1    Sep. 11, 2003

Related U.S. Application Data

(60) Provisional application No. 60/295,153, filed on Jun. 1, 2001.

(51) Int. Cl.
*A61K 48/00*    (2006.01)
*A01N 63/00*    (2006.01)

(52) U.S. Cl. .................................................... 424/93.2

(58) Field of Classification Search ............. 435/320.1; 536/23.1, 23.5; 424/93.2
See application file for complete search history.

(56) References Cited

U.S. PATENT DOCUMENTS

| | | | |
|---|---|---|---|
| 2,465,357 A | 3/1949 | Correll et al. | |
| 3,955,719 A | 5/1976 | Pheulpin | |
| 4,191,747 A | 3/1980 | Scheicher | |
| 4,294,753 A | 10/1981 | Urist | |
| 4,394,370 A | 7/1983 | Jefferies | |
| 4,399,216 A | 8/1983 | Axel et al. | |
| 4,419,446 A | 12/1983 | Howley et al. | |
| 4,434,094 A | 2/1984 | Seyedin et al. | |
| 4,441,915 A | 4/1984 | Arndt et al. | |
| 4,455,256 A | 6/1984 | Urist | |
| 4,468,464 A | 8/1984 | Cohen et al. | |
| 4,472,840 A | 9/1984 | Jefferies | |
| 4,553,542 A | 11/1985 | Schenck et al. | |
| 4,563,350 A | 1/1986 | Nathan et al. | |
| 4,596,574 A | 6/1986 | Urist | |
| 4,608,199 A | 8/1986 | Caplan et al. | |
| 4,619,989 A | 10/1986 | Urist | |
| 4,627,982 A | 12/1986 | Seyedin et al. | |
| 4,642,120 A | 2/1987 | Nevo et al. | |
| 4,662,884 A | 5/1987 | Stensaas et al. | |
| 4,681,763 A | 7/1987 | Nathanson et al. | |
| 4,703,008 A | 10/1987 | Lin | |
| 4,727,028 A | 2/1988 | Santerre et al. | |
| 4,737,578 A | 4/1988 | Evans et al. | |
| 4,758,233 A | 7/1988 | Phillips et al. | |
| 4,761,471 A | 8/1988 | Urist | |
| 4,766,067 A | 8/1988 | Biswas | |
| 4,767,628 A | 8/1988 | Hutchinson | |
| 4,769,328 A | 9/1988 | Murray et al. | |
| 4,774,228 A | 9/1988 | Seyedin et al. | |
| 4,774,322 A | 9/1988 | Seyedin et al. | |
| 4,784,055 A | 11/1988 | Langen et al. | |
| 4,789,732 A | 12/1988 | Urist | |
| 4,795,804 A | 1/1989 | Urist | |
| 4,798,885 A | 1/1989 | Mason et al. | |
| 4,804,744 A | 2/1989 | Sen | |
| 4,810,691 A | 3/1989 | Seyedin et al. | |
| 4,828,990 A | 5/1989 | Higashi et al. | |
| 4,843,063 A | 6/1989 | Seyedin et al. | |
| 4,851,521 A | 7/1989 | della Valle et al. | |
| 4,868,161 A | 9/1989 | Robert | |
| 4,877,864 A | 10/1989 | Wang et al. | |
| 4,886,747 A | 12/1989 | Derynck et al. | |
| 4,908,204 A | 3/1990 | Robinson et al. | |
| 4,920,962 A | 5/1990 | Proulx | |
| 4,923,805 A | 5/1990 | Reddy et al. | |
| 4,955,892 A | 9/1990 | Daniloff | |
| 4,963,146 A | 10/1990 | Li | |
| 4,968,590 A | 11/1990 | Kuberasampath et al. | |
| 4,992,274 A | 2/1991 | Robinson et al. | |
| 5,011,486 A | 4/1991 | Aebischer et al. | |
| 5,011,691 A | 4/1991 | Oppermann et al. | |
| 5,013,649 A | 5/1991 | Wang et al. | |
| 5,019,087 A | 5/1991 | Nichols | |
| 5,024,841 A | 6/1991 | Chu et al. | |
| 5,026,381 A | 6/1991 | Li | |

(Continued)

FOREIGN PATENT DOCUMENTS

EP    0 052 510    5/1982

(Continued)

OTHER PUBLICATIONS

Kawamura, Blood. Sep. 15, 2000;96:2005-11.*

(Continued)

*Primary Examiner*—Brian Whiteman
(74) *Attorney, Agent, or Firm*—Finnegan, Henderson, Farabow, Garrett + Dunner LLP

(57) ABSTRACT

Compositions and methods for systemic administration of DNA encoding bone morphogenic proteins for promotion of osteogenesis are disclosed. The compositions and methods of the invention may be utilized for fracture repair. The invention further discloses compositions and methods for systemic administration of bone morphogenetic proteins for promotion of osteogenesis. These compositions and methods may be used in bone fracture healing and repair. These composition of the invention may be further utilized in increasing bone mineral density.

4 Claims, 1 Drawing Sheet

U.S. PATENT DOCUMENTS

| | | |
|---|---|---|
| 5,041,538 A | 8/1991 | Ling et al. |
| 5,071,834 A | 12/1991 | Burton et al. |
| 5,089,396 A | 2/1992 | Mason et al. |
| 5,102,807 A | 4/1992 | Burger et al. |
| 5,106,626 A | 4/1992 | Parsons et al. |
| 5,106,748 A | 4/1992 | Wozney et al. |
| 5,108,753 A | 4/1992 | Kuberasampath et al. |
| 5,108,922 A | 4/1992 | Wang et al. |
| 5,116,738 A | 5/1992 | Wang et al. |
| 5,118,667 A | 6/1992 | Adams et al. |
| 5,124,316 A | 6/1992 | Antoniades et al. |
| 5,141,905 A | 8/1992 | Rosen et al. |
| 5,147,399 A | 9/1992 | Dellon et al. |
| 5,166,058 A | 11/1992 | Wang et al. |
| 5,166,190 A | 11/1992 | Mather et al. |
| 5,166,322 A | 11/1992 | Shaw et al. |
| 5,168,050 A | 12/1992 | Hammonds et al. |
| 5,171,579 A | 12/1992 | Ron et al. |
| 5,187,086 A | 2/1993 | Janda |
| 5,187,263 A | 2/1993 | Murray et al. |
| 5,202,120 A | 4/1993 | Silver et al. |
| 5,206,028 A | 4/1993 | Li |
| 5,208,219 A | 5/1993 | Ogawa et al. |
| 5,215,893 A | 6/1993 | Mason et al. |
| 5,216,126 A | 6/1993 | Cox et al. |
| 5,217,867 A | 6/1993 | Evans et al. |
| 5,218,090 A | 6/1993 | Connors |
| 5,229,495 A | 7/1993 | Ichijo et al. |
| 5,256,418 A | 10/1993 | Kemp et al. |
| 5,258,494 A | 11/1993 | Oppermann et al. |
| 5,266,683 A | 11/1993 | Oppermann et al. |
| 5,278,145 A | 1/1994 | Keller et al. |
| 5,284,756 A | 2/1994 | Grinna et al. |
| 5,286,654 A | 2/1994 | Cox et al. |
| 5,290,271 A | 3/1994 | Jernberg |
| 5,292,802 A | 3/1994 | Rhee et al. |
| 5,306,307 A | 4/1994 | Senter et al. |
| 5,308,889 A | 5/1994 | Rhee et al. |
| 5,324,519 A | 6/1994 | Dunn et al. |
| 5,324,775 A | 6/1994 | Rhee et al. |
| 5,328,955 A | 7/1994 | Rhee et al. |
| 5,352,715 A | 10/1994 | Wallace et al. |
| 5,354,557 A | 10/1994 | Oppermann et al. |
| 5,356,629 A | 10/1994 | Sander et al. |
| 5,364,839 A | 11/1994 | Gerhart et al. |
| 5,366,875 A | 11/1994 | Wozney et al. |
| 5,399,346 A | 3/1995 | Anderson et al. |
| 5,399,677 A | 3/1995 | Wolfman et al. |
| 5,405,390 A | 4/1995 | O'Leary et al. |
| 5,411,941 A | 5/1995 | Grinna et al. |
| 5,413,989 A | 5/1995 | Ogawa et al. |
| 5,420,243 A | 5/1995 | Ogawa et al. |
| 5,422,340 A | 6/1995 | Ammann et al. |
| 5,447,725 A | 9/1995 | Damani et al. |
| 5,455,041 A | 10/1995 | Genco et al. |
| 5,455,329 A | 10/1995 | Wingender et al. |
| 5,457,047 A | 10/1995 | Wingender et al. |
| 5,457,092 A | 10/1995 | Schluter et al. |
| 5,459,047 A | 10/1995 | Wozney et al. |
| 5,464,440 A | 11/1995 | Johansson |
| 5,508,263 A | 4/1996 | Grinna et al. |
| 5,516,654 A | 5/1996 | Israel |
| 5,520,923 A | 5/1996 | Tjia et al. |
| 5,538,892 A | 7/1996 | Donahoe et al. |
| 5,543,394 A | 8/1996 | Wozney et al. |
| 5,545,616 A | 8/1996 | Woodruff |
| 5,547,854 A | 8/1996 | Donahoe et al. |
| 5,556,767 A | 9/1996 | Rosen et al. |
| 5,618,924 A | 4/1997 | Wang et al. |
| 5,631,142 A | 5/1997 | Wang et al. |
| 5,635,372 A | 6/1997 | Celeste et al. |
| 5,635,373 A | 6/1997 | Wozney et al. |
| 5,637,480 A | 6/1997 | Celeste et al. |
| 5,639,638 A | 6/1997 | Wozney et al. |
| 5,645,592 A | 7/1997 | Nicolais et al. |
| 5,648,467 A | 7/1997 | Trinchieri et al. |
| 5,650,176 A | 7/1997 | Lee et al. |
| 5,650,494 A | 7/1997 | Cerletti et al. |
| 5,658,882 A | 8/1997 | Celeste et al. |
| 5,661,007 A | 8/1997 | Wozney et al. |
| 5,674,292 A | 10/1997 | Tucker et al. |
| 5,674,844 A | 10/1997 | Kuberasampath et al. .... 514/12 |
| 5,688,678 A | 11/1997 | Hewick et al. |
| 5,693,779 A | 12/1997 | Moos, Jr. et al. |
| 5,700,664 A | 12/1997 | Yang et al. |
| 5,700,774 A | 12/1997 | Hattersley et al. |
| 5,700,911 A | 12/1997 | Wozney et al. |
| 5,703,043 A | 12/1997 | Celeste et al. |
| 5,728,679 A | 3/1998 | Celeste et al. |
| 5,750,651 A | 5/1998 | Oppermann et al. |
| 5,752,974 A | 5/1998 | Rhee et al. |
| 5,756,457 A | 5/1998 | Wang et al. |
| 5,786,217 A | 7/1998 | Tubo et al. |
| 5,813,411 A | 9/1998 | Van Bladel et al. |
| 5,827,733 A | 10/1998 | Lee et al. |
| 5,843,742 A * | 12/1998 | Natsoulis et al. ........... 435/465 |
| 5,846,931 A | 12/1998 | Hattersley et al. |
| 5,849,880 A | 12/1998 | Wozney et al. |
| 5,866,364 A | 2/1999 | Israel et al. |
| 5,932,216 A | 8/1999 | Celeste et al. |
| 5,935,594 A | 8/1999 | Ringeisen et al. |
| 5,936,067 A | 8/1999 | Graham et al. |
| 5,939,323 A | 8/1999 | Valentini et al. |
| 5,939,388 A | 8/1999 | Rosen et al. |
| 5,942,496 A * | 8/1999 | Bonadio et al. ............. 514/44 |
| 5,965,403 A | 10/1999 | Celeste et al. ............. 435/69.4 |
| 5,972,368 A | 10/1999 | McKay |
| 5,986,058 A | 11/1999 | Lee et al. |
| 6,001,352 A | 12/1999 | Boyan et al. |
| 6,004,937 A | 12/1999 | Wood et al. |
| 6,027,742 A | 2/2000 | Lee et al. |
| 6,027,919 A | 2/2000 | Celeste et al. |
| 6,034,061 A | 3/2000 | Rosen et al. |
| 6,034,062 A | 3/2000 | Thies et al. |
| 6,132,214 A | 10/2000 | Suhonen et al. |
| 6,150,328 A | 11/2000 | Wang et al. |
| 6,177,406 B1 | 1/2001 | Wang et al. |
| 6,187,742 B1 | 2/2001 | Wozney et al. |
| 6,190,880 B1 | 2/2001 | Israel et al. |
| 6,207,813 B1 | 3/2001 | Wozney et al. |
| 6,245,889 B1 | 6/2001 | Wang et al. |
| 6,284,872 B1 | 9/2001 | Celeste et al. |
| 6,287,816 B1 | 9/2001 | Rosen et al. |
| 6,291,206 B1 | 9/2001 | Wozney et al. |
| 6,303,362 B1 * | 10/2001 | Kay et al. .................... 514/44 |
| 6,331,612 B1 | 12/2001 | Celeste et al. |
| 6,340,668 B1 | 1/2002 | Celeste et al. |
| 6,432,919 B1 | 8/2002 | Wang et al. |
| 6,437,111 B1 | 8/2002 | Wozney et al. |
| 6,558,925 B2 | 5/2003 | Graham et al. |
| 6,586,388 B2 | 7/2003 | Oppermann et al. |
| 6,593,109 B1 | 7/2003 | Israel et al. |
| 6,610,513 B2 | 8/2003 | Wozney et al. |
| 6,613,563 B1 * | 9/2003 | Sosnowski et al. ...... 435/320.1 |
| 6,613,744 B2 | 9/2003 | Wozney et al. |
| 6,623,934 B2 | 9/2003 | Celeste et al. |
| 6,699,471 B2 | 3/2004 | Radice et al. |
| 6,719,968 B2 | 4/2004 | Celeste et al. |

FOREIGN PATENT DOCUMENTS

| | | |
|---|---|---|
| EP | 0 058 481 | 8/1982 |
| EP | 0 061 840 | 10/1982 |
| EP | 0 121 976 | 10/1984 |

| | | |
|---|---|---|
| EP | 0 128 041 | 12/1984 |
| EP | 0 155 476 | 9/1985 |
| EP | 0 169 016 | 1/1986 |
| EP | 0 177 343 | 4/1986 |
| EP | 0 212 474 | 3/1987 |
| EP | 0 222 491 | 5/1987 |
| EP | 0 241 809 | 10/1987 |
| EP | 0 313 578 | 5/1989 |
| EP | 0 329 239 | 8/1989 |
| EP | 0 394 418 | 10/1990 |
| EP | 0 401 055 | 12/1990 |
| EP | 0 409 472 | 1/1991 |
| EP | 0 416 578 | 3/1991 |
| EP | 0 429 570 | 6/1991 |
| EP | 0 433 225 | 6/1991 |
| EP | 0 512 844 | 11/1992 |
| EP | 0 530 804 | 3/1993 |
| EP | 0 531 448 | 3/1993 |
| EP | 0 336 394 | 7/1994 |
| EP | 0 626 451 | 11/1994 |
| EP | 0 741 187 | 11/1996 |
| EP | 0 592 562 | 11/1999 |
| EP | 0 536 186 | 11/2001 |
| EP | 0 688 869 | 3/2003 |
| EP | 0 831 884 | 7/2003 |
| JP | 05-123390 | 5/1993 |
| JP | N05-277174 A2 | 10/1993 |
| WO | WO 84/01106 | 3/1984 |
| WO | WO 85/04173 | 9/1985 |
| WO | WO 86/00525 | 1/1986 |
| WO | WO 86/00639 | 1/1986 |
| WO | WO 87/00528 | 1/1987 |
| WO | WO 88/00205 | 1/1988 |
| WO | WO 89/09787 | 10/1989 |
| WO | WO 89/09788 | 10/1989 |
| WO | WO 89/10133 | 11/1989 |
| WO | WO 89/10409 | 11/1989 |
| WO | WO 90/03733 | 4/1990 |
| WO | WO 90/11366 | 10/1990 |
| WO | WO 91/02744 | 3/1991 |
| WO | WO 91/04274 | 4/1991 |
| WO | WO 91/05802 | 5/1991 |
| WO | WO 91/10444 | 7/1991 |
| WO | WO 91/17777 | 11/1991 |
| WO | WO 91/18047 | 11/1991 |
| WO | WO 91/18098 | 11/1991 |
| WO | WO 92/05198 | 4/1992 |
| WO | WO 92/05199 | 4/1992 |
| WO | WO 92/07004 | 4/1992 |
| WO | WO 92/07073 | 4/1992 |
| WO | WO 92/09697 | 6/1992 |
| WO | WO 92/14481 | 9/1992 |
| WO | WO 92/15323 | 9/1992 |
| WO | WO 92/20793 | 11/1992 |
| WO | WO 92/22319 | 12/1992 |
| WO | WO 93/00049 | 1/1993 |
| WO | WO 93/00050 | 1/1993 |
| WO | WO 93/00432 | 1/1993 |
| WO | WO 93/04692 | 3/1993 |
| WO | WO 93/05751 | 4/1993 |
| WO | WO 93/06872 | 4/1993 |
| WO | WO 93/09229 | 5/1993 |
| WO | WO 93/09802 | 5/1993 |
| WO | WO 93/13206 | 7/1993 |
| WO | WO 93/16099 | 8/1993 |
| WO | WO 93/19177 | 9/1993 |
| WO | WO 93/20858 | 10/1993 |
| WO | WO 94/01557 | 1/1994 |
| WO | WO 94/03200 | 2/1994 |
| WO | WO 94/06449 | 3/1994 |
| WO | WO 94/11502 | 5/1994 |
| WO | WO 94/15949 | 7/1994 |
| WO | WO 94/15965 | 7/1994 |
| WO | WO 94/15966 | 7/1994 |
| WO | WO 94/21681 | 9/1994 |
| WO | WO 94/24285 | 10/1994 |
| WO | WO 94/26892 | 11/1994 |
| WO | WO 94/26893 | 11/1994 |
| WO | WO 95/01801 | 1/1995 |
| WO | WO 95/01802 | 1/1995 |
| WO | WO 95/05846 | 3/1995 |
| WO | WO 95/07982 | 3/1995 |
| WO | WO 95/10539 | 4/1995 |
| WO | WO 95/10611 | 4/1995 |
| WO | WO 95/12664 | 5/1995 |
| WO | WO 95/15966 | 6/1995 |
| WO | WO 95/16035 | 6/1995 |
| WO | WO 95/18856 | 7/1995 |
| WO | WO 95/33830 | 12/1995 |
| WO | WO 96/01845 | 1/1996 |
| WO | WO 96/02559 | 2/1996 |
| WO | WO 96/16668 | 6/1996 |
| WO | WO 96/18924 | 6/1996 |
| WO | WO 96/26710 | 9/1996 |
| WO | WO 96/38570 | 12/1996 |
| WO | WO 96/39170 | 12/1996 |
| WO | WO 96/39203 | 12/1996 |
| WO | WO 96/40883 | 12/1996 |
| WO | WO 94/05800 | 3/1997 |
| WO | WO 97/15321 | 5/1997 |
| WO | WO 97/22308 | 6/1997 |
| WO | WO 97/34626 | 9/1997 |
| WO | WO 97/40137 | 10/1997 |
| WO | WO 97/45532 | 12/1997 |
| WO | WO 97/48275 | 12/1997 |
| WO | WO 97/49412 | 12/1997 |
| WO | WO 98/16641 | 4/1998 |
| WO | WO 98/31788 | 7/1998 |
| WO | WO 98/34951 | 8/1998 |
| WO | WO 98/40113 | 9/1998 |
| WO | WO 98/40508 | 9/1998 |
| WO | WO 98-40508 A | 9/1998 |
| WO | WO 98/49296 | 11/1998 |
| WO | WO 99/01159 | 1/1999 |
| WO | WO 99/24070 | 5/1999 |
| WO | WO 99/31120 | 6/1999 |
| WO | WO 99/37320 | 7/1999 |
| WO | WO 99/38543 | 8/1999 |
| WO | WO 99/45949 | 9/1999 |
| WO | WO 99/47177 * | 9/1999 |
| WO | WO 00/37124 | 6/2000 |
| WO | WO 00/43781 A | 7/2000 |
| WO | WO 01/28602 A | 4/2001 |
| WO | WO 02/43759 | 6/2002 |

OTHER PUBLICATIONS

Drozdoff et al. PNAS, 91, 5528-5532, 1994.*
Kameda et al. Develop. Growth. Differ., 42:229-236, Jun. 2000.*
Basic-Koretic, M. et al. "BMP-6 Restores Lost Bone," *Bone OR67*: Jun. 5-10, 2001-1st Joint Meeting of the International Bone and Mineral Society and the European Calcified Tissue Society.
Buljan-Culej, J. et al. "Bone Morphogenetic Protein-6 Restores Lost Bone in Ovariectomized Rats," *Calcif. Tissue Int.* 70: P-136 (Apr. 2002).
Alden et al., "In Vivo Endochondral Bone Formation Using a Bone Morphogenetic Protein 2 Adenoviral Vector," *Human Gene Therapy*, 10: 2245-2253 (1999).
European Search Report for 02734594.1-2103 dated Dec. 20, 2005.
Fang et al., "Stimulation of new bone formation by direct transfer of osteogenic plasmid genes," *Proc. Natl. Acad. Sci. U.S.A.*, 93:5753-5758 (1996).
Gitelman et al., "Recombinant Vgr-1/BMP-6-expressing Tumors Induce Fibrosis and Endochrondral Bone Formation In Vivo," *Journal of Cell Biology*, 126:1595-1609 (1994).

Gitelman et al., "Vgr-1/BMP-6 Induces Osteoblastic Differentiation of Pluripotential Mesenchymal Cells," *Cell Growth and Differentiation, The Association*, Philadelphia, PA, 6:827-836 (1995).

XP002355901 Abstract "The use of bone morphogenetic protein gene therapy in craniofacial bone repair," Medline online database, Accession No. NLM11314095 (2000).

XP002355902 Abstract "Ectopic osteogenesis using adenoviral bone morphogenetic protein (BMP)-4 and BMP-6 gene transfer," Medline online database, Accession No. NLM12377187 (2002).

Jelic et al., "Regeneration of Articular Cartilage Chondral Defects by Osteogenic Protein-1 (Bone Morphogenetic Protein-7) in Sheep," *Growth Factors*, 19: 101-113 (2001).

Pluhar et al., "The effect of recombinant human bone morphogenetic protein-2 on femoral reconstruction with an intercalary allograft in a dog model," *J. Orthop. Res.*, 19:308-317 (2001).

Saito et al., "Biodegradable Poly-D, I-Lactic Acid Polyethylene Glycol Block Copolymers as a BMP Delivery System for Inducing Bone," *J. Bone Joint Surg. Am.*, 83-A:S1 92-98 (2001).

Alba et al., Blood, 90:3923-3030 (1997).
Alberts et al., Molecular Biology of the Cell, Third Ed., Garland Publishing, Inc., New York, NY, pp. 1142 (1983).
Alden et al., Human Gene Therapy, 13:2245-2253 (1999).
Alden et al., Medline online database, Accession No. NLM11314095 (2000).
Amizuka et al., J. Cell Biol., 126:1611-1623 (1994).
Aral et al., OsteoArthritis and Cartilage, 12:599-613 (2004).
Attisano et al., Cell, 68:97-108 (1992).
Baird et al., Biochem. Biophys. Res. Comm., 138:476-482 (1986).
Barka et al., J. Histochem. Cytochem., 52(4):469-77 (2004).
Barres. B.A. et al., Development, 118:283-295 (1993).
Basler, K. et al., Cell, 73:687-702 (1993).
Beauchef et al., Biochemical and Biophysical Research Communications, 333:1123-1131 (2005).
Beck et al., Growth Factors, 2:273-282 (1990).
Belo et al., Mech. Devel., 68:45-57 (1997).
Bendig, Genetic Engineering, 7:91-127 (1998).
Berndsen et al., Eur. Surg. Res., 36(5):318-22 (2004).
Bernstein, et al., Dermatol. Surg., 23(9):785-799 (1997).
Bi et al., Nat. Genet., 22(1):85-9 (1999).
Biben et al., Develop. Biol., 194:135-151.
Bignami, A. et al., Brain Res., 43:429-435 (1972).
Bignami, A. et al., Plasticity and Regeneration of the Nervous System, 197-206 (1991).
Blessing et al., Genes & Dev., 7:204-215 (1993).
Bleul et al., J. Immun., 175:5213-5221 (2005).
Boese et al., Methods Enzymol., 392:73-96 (2005).
Bolton et al., Biochem J., 144:529 (1973).
Border et al., J. Clin. Invest., 90:1-7 (1992).
Botchkarev, V. A., J. Invest. Dermatol., 120(1):36-47 (2002).
Botchkarev et al., Differentiation, 72:512-526 (2004).
Botchkarev et al., Nature Cell Biol., 1:158-164 (1999).
Botchkarev et al., FASEB Journal, 15:2205-2214 (2001).
Bouwmeester et al., Nature, 382:595-601 (1996).
Bowen-Pope et al., J. Biol. Chem., 237:5161 (1982).
Bowie et al., Science, 247:1306-1310 (1990).
Brown et al., J. Am. Osteopath. Assoc., 104(S2):S11-S16 (2004).
Brown et al., J. Immunol., 142:679 (1989).
Broxmeyer et al., PNAS, 85:9052 (1988).
Bruder et al., J. Cell Biochem., 56:283-294 (1994).
Burt, D.W., BBRC, 184:590-595 (1992).
Callahan et al., Current Opinion in Genetics & Dev., 11:541-546 (2001).
Campoccia et al., Biomaterials, 19:2101-27 (1998).
Canalis. Endocrinology, 118(1):74-81 (1986).
Caplan, A., Bone Repair and Regeneration, 21:429-435 (1994).
Celeste et al., J. Bone Mineral Res., 9:suppl. 5136 (1994).
Celeste et al., PNAS, 87:9843-9847 (1990).
Chang et al., J. Biol. Chem., 269:28227-28234 (1994).
Cheah et al., Proc Natl Acad Sci., 82(9):2555-9 (1985).
Chen et al., Hypertension, 47:230-237 (2006).
Chen et al., Cell Research, 14(6):441-449 (2004).
Clark et al., Expert Opin. Ther. Targets, 7(1):19-34 (2003).

Conlon et al., Development, 120:1919 (1994).
Conlon et al., Development, 111:969 (1991).
Collignon et al., Nature, 381:155 (1996).
Cook et al., Clin. Orth. and Related Research., 324:29-38 (1996).
Cotsarelis et al., TRENDS in Mol. Med., 7(7):293-301 (2001).
Creighton, T.E., Proteins: Structure and Molecular Principles, W.H. Freeman and Co., New York (1983).
Cunningham et al., PNAS, 89:11740-11744 (1992).
Dagert et al., Gene, 6:23 (1979).
Dale et al., EMBO J., 12:4471 (1993).
D'Alessandro et al., Growth Factors, 11:53-69 (1994).
d'Allesandro et al., J. Bone Mineral Res., (6) Suppl: 1:S153 (1991).
DeWulf et al., Nature, 344:380 (1990).
Dexter et al., Nature, 344:380 (1990).
DiLeone et al., Genetics, 148:401-408 (1998).
Dlugosz, A., J. Clinical Investigation, 104(7):851-853 (1999).
Doctor et al., Dev. Biol., 151:591-605 (1992).
Doege et al., Extracellular Matrix Genes (Sandel, L. J.; Boyd, C. D., eds.) Academic Press (New York) 137-152 (1990).
Dormois et al., Am. Heart J., 90:360-368 (1975).
Ducy et al., Kidney Intl., 57:2207-2214 (2000).
Dunn et al., Cancer Cells, 3:227-234 (1985).
Ebner et al., Science, 260:1344-1348 (1993).
Edge et al., Anal Biochem., 118:131-137 (1981).
Elhammer et al., Glycoconjugate J., 16:171-180 (1999).
Ellis et al., Expert Reviews in Mol. Med., p. 1-10 (Nov. 2002).
Estevez et al., Nature, 365:644-649 (1993).
Eto et al., Biochem. Biophys. Res. Comm., 142:1095 (1987).
Fainsod et al., Mech Dev., 1:39-50 (1997).
Fallon et al., J. Cell Biol., 100:198-207 (1985).
Fenton et al., Endocrinology, 129:1762-1768 (1991).
Finch et al., PNAS, 94:6770-6775 (1997).
Fleisch, Bisphosphonates In Disease, From the Laboratory to the Patient, 3rd Ed. Parthenon Publishing (1997).
Foitzik et al., FASEB Journal, 14:752-760 (2000).
Foley, P.A., Brit. Med. J. 320:850-853 (2000).
Forslund et al., J. Orth. Res., 21:617-621 (2003).
Freireich et al., Cancer Chemother Reports, 50(4):219-244 (1966).
Frischauf et al., J. Mol. Biol., 170:827-842 (1983).
Frommel et al., J. Mol. Evol., 24:233-257 (1985).
Fukai et al., Dev. Biol. 159:131-139 (1993).
Fukui et al., Dev. Biol., 159:131-139 (1993).
Gamer et al., Develop. Biol. 208:222-232 (1999).
Garrett et al., J. Clinical Investigation, 111(11):1771-1782 (2003).
Geisert et al., Develop. Biol., 143:335-345 (1991).
Gerhart et al., Trans. Othop. Res. Soc., 16:172 (1991).
Gething et al., Nature, 293:620-625 (1981).
Gilbert. American Journal of Knee Surgery, (11)1:42-46 (1998).
Gittens et al., J. Controlled Release, 98: 255-256 (2004).
Gittens et al., Pharmaceutical Research, 7: 978-987 (2003).
Goddard et al., Current Opinion in Biotechnology, 15:314-322(2004).
Goddard et al., Trends in Biotechnology, 22(7):363-370 (2004).
Goodman, R., Methods for Serum-Free Culture of Neuronal and Lymphoid Cells, 23-36 (1984).
Gosalia et al., PNAS, 100(15):8721-8726 (2003).
Gotoh et al., J. Biol. Chem., 277(41):38189-38196 (2002).
Gotoh et al., J. Biol. Chem., 277(41):38179-38188 (2002).
Gough et al., EMBO J., 4:645-653 (1985).
Graham et al., EMBO, 15:6505-6515 (1996).
Graham et al., Growth Factors, 7:151-160 (1992).
Graham et al., J. Biol. Chem., 269:4974-4978 (1994).
Graham et al., Nature, 344:442 (1990).
Guigon et al., Chem. Abstracts, 96:36, Abstract No. 115633h (1982).
Guigon et al., Cancer Res., 42:638 (1982).
Hammonds et al., Mol. Endocrin., 5:149-155 (1991).
Hannon et al., Nature, 418:244-251 (2002).
Harrison et al., Exp. Cell Res., 92:340-345 (1991).
Hasimoto et al., J. Biol. Chem., 267:7203-7206 (1992).
Hayder et al., J. Immul., 163:1516-20 (1999).
He et al., Develop. Dynamics, 196:133-142 (1993).
He et al., Oncogene, 24:3054-3058 (2005).

Heasman et al., Dev. Biol., 243:209-214 (2002).
Hebda et al., J. Invest. Dermatol., 91:440-445 (1988).
Hefti et al., J. Neurobiol., 25:1418-1435 (1994).
Helm et al., J. Neurosurg., 95:298-307 (2001).
Helm et al., J. Am. Chem. Soc., 125:11168-11169 (2003).
Hemmati-Brinvanlou et al., Nature, 359:609-614 (1992).
Hoang et al., J. Biol. Chem., 271:26131-26137 (1996).
Holinagel et al., Calcigied Tissue Int'l, 56:430 (1995).
Hoodless et al., Curr. Topics Microbiol. Immunol., 228:235-272 (1998).
Hu et al., Chem. & Biol., 9:1287-1296 (2002).
Hunkaplller et al., Met. Enzymol., 91:399-413 (1983).
Ikeda et al., J. Bone Mner. Metab., 22:337-340 (2005).
Inada et al., Biochem. Biophys. Res. Comm., 222:317-22 (1996).
Inouye et al., Mol. Cell. Endocrinol., 90:1 (1992).
Iwasaki, J. Biol. Chem., 271:17360-5 (1996).
Jane et al., Medline online database, Accession No. NLM12377187 (2002).
Janowska-Wieczorek et al., Biol. Abstracts, Reviews-Reports-Meetings, 33:61402 (1987).
Jones et al., Mol. Endocrinol. 6:1961-1968 (1992).
Jones et al., Development, 111:531-542 (1991).
Jonhagen et al., Dement. Cogn. Disord., 9:246-257 (1998).
Joyce et al., J. Cell Biochem., Suppl.17E:136, Abstract R504 (1993).
Kalish, et al, J. Invest. Dermatol., 8(2):164-167 (2003).
Kalyani et al., J. Neuroscience, 18:7856-7869 (1998).
Karaplis et al., Mol. Endocrin., 4:441-446 (1990).
Karaplis et al., Genes & Development, 8:277-289 (1994).
Katagiri et al., J. Cell Biol., 127:1755-1766 (1994).
Kaufman et al., Mol. Cell Biol., 2:1304-1319 (1982).
Kaufman et al., Mol. Cell Biol., 5:1750-1759 (1985).
Kaufman et al., J. Mol. Biol., 159:601-629 (1982).
Kaufman et al., PNAS, 82:689-693 (1985).
Khan et al., *Sports Med 27*:393-408 (1999).
Kingsley et al., Cell, 71:399-410 (1992).
Kingsley et al., Genes & Development, 8:133-146 (1994).
Kirn-Safran et al., Birth Defects Res., 72(Part C):69-88 (2004).
Klein-Nulend et al., Tissue Engineering, 4:305-313 (1998).
Klein et al., Brain Res. 875:144-151 (2000).
Kliot et al., Exper. Neur., 109:57-69 (1990).
Knudson et al., Sem Cell Dev. Biol., 12:69-78 (2001).
Koenig et al., Mol. Cell Biol., 14:5961-5974 (1994).
Koopman et al., JBC, 273:33267-33272 (1998).
Krom et al., BMC Biotech 6(11):[e-published ahead of print].
Kronenberg, H., Nature, 423:332-336 (2003).
Krueger, G.G., N.E.J. Med., 328:1845-1846 (1993).
Kulessa et al., EMBO Journal, 19(24):6664-6674 (2000).
Ladner et al., Dev. Biol., 218:183-198 (2000).
LaPan et al., Program and Abstract, 13th Ann. Mtg of the AM Society of Bone and Min. Res., 8/24-28, p. 5153, Abstract No. 280, Mary Ann Liebert, Inc. NY (1991).
Lathe, J., J. Mol. Biol., 183:1-12 (1985).
Lawn et al., Cell, 15:1157-1174 (1978).
Lefer et al., PNAS, 90:1018-22 (1993).
LeMaire et al., Trends in Genetics, 12:525-531 (1996).
Leslie M., Nurse Practitioner, 24:38, 41-8 (1999).
Lewin, Science, 237:1570 (1987).
Leyns et al., Cell, 88:747-756 (1997).
Lin et al., Cell, 68:775-785 (1992).
Lin et al., Science, 260:1130-1132 (1993).
Lipes et al., PNAS, 85:9704 (1988).
Liu et al., Mol. Genet. Genomics, 266(4): 614-623 (2001).
Lodish et al., Mol. Cell Biol., 3rd Ed., W.H. Freeman & Co., p. 266 (1995).
Lopez-Coviella et al., J. Physiol. Paris., 92:460-461 (1998).
Lopez-Coviella et al., Science, 289:313-316 (2000).
Lopez-Coviella et al., Xth International Symposium on Cholinergic Mechanisms (1998).
Lopez-Coviella et al., Soc. Neurosci. Abstracts, 25:517 (1999).
Lord et al., Brit J. Haematol., 34:441 (1976).
Lorimore et al., Leuk. Res., 14:481-489 (1990).
Lou, J., Clinical Orthopaedics and Related Research, 379S:S252-S255 (2000).
Lou et al., J. Orth. Research, 19:1199-1202 (2001).
Lowe et al., Nature, 381:158 (1996).
Lucas et al., Differentiation, 37:47-52 (1988).
Luthman et al., Nucl. Acids Res., 11:1295-1308 (1983).
Luyten et al., J. Biol. Chem., 264:13377-13380 (1989).
Luyten et al., Exp. Cell. Res., 210(2):224-229 (1994).
Lyons et al., PNAS, 86:4554-4558 (1989).
MacDonald, N., Dermatol. Nurs., 11:356-359 (1999).
Mangin et al., PNAS, 85:597-601 (1988).
Mangin et al., Gene, 95:195-202 (1990).
Maniatis et al., Mol. Cloning, A Laboratory Manual, Cold Spring Harbor Laboratory, CSH, N.Y.:310-323, 387-389 & 404-433 (1982).
Mantel et al., PNAS, 90:2232-236 (1993).
Mansour et al., J. Neurosci. Res., 25:300-377 (1990).
Marieb, E.N., In Human Anatomy and Physiology, 2nd Ed., The Benjamin/Cummings Publishing Co., pp. 373-375 (1992).
Mark, J. Cell. Biol., 130:701-10 (1995).
Marra et al., EMBL Database, Accession No. AA120122 (1996).
Martin et al., Crit. Rev. Biochem. Mol. Biol., 26:377-395 (1991).
Mason et al., Nature, 318:659-663 (1985).
Massague et al., Trends in Cell Biol., 4:172-178 (1994).
Massague et al., Cell, 69:1067-1070 (1992).
Massague et al., Cell, 49:437-438 (1987).
Massagué et al., Genes & Development, 14:627-644 (2000).
Mathews et al., Cell, 65:973-982 (1991).
Matsuzaki et al., J. Biol. Chem., 268:12719-12723 (1993).
Matzuk et al., Nature, 360:313 (1992).
McConahey et al., Int. Arch. Allergy, 29:185-189 (1966).
McDonald et al., Cell, 73:421-424 (1993).
McManus et al., Nat. Reviews, 3:737-747 (2002).
Mehta et al., J. Hand. Surgery, (30A)1: 136-141 (2005).
Messenger, A.G. et al., Brit. J. Dermatol., 150:186-194 (2004).
Michos et al., Development, 131:3401-3410 (2004).
Miller et al., J. Immunol., 143:2907 (1989).
Miller et al., Genetic Engineering, 8:277-298 (1986).
Miyazono et al., Gen Bank Record No. Z23154 (1993).
Morii et al., J. Biol. Chem., 258:12749-12752 (1983).
Mullins et al., Nature, 303:856-858 (1984).
Nabeshima et al., Alz Dis. And Assoc. Disord. 14 (Supple. 1):S39-S46 (2000).
Nakamura et al., J. Biol. Chem., 267:18924-18928 (1992).
Nakamura et al., Biol. Pharm. Bull., 28(3):429-433 (2005).
Nakao et al., Mol. Cell Biol., 10:3646-3658 (1990).
Nakatani T., Jap. J. Clin. Med., 52:824-33 (1994).
Narimatsu et al., Glycoconjugate J., 21:17-24 (2004).
Nathan et al., J. Cell Biol., 113:981-986 (1991).
National Institutes of Health, *Questions & Answers About Atopecia Areata* (2003).
Neuhaus et al., Mech. Dev., 80;181-184 (1999).
Nirschl, R., American Orthopaedic Society for Sports Medicine, Leadbetter, W. et al., eds, Ch. 13:577-585 (1989).
Ngo et al., Merz et al., eds., Brickhauser, Boston, Springer Verlag, pp. 433-434 & 492-495 (1994).
Noble et al., J. Neuroscience, 4:1892-1903 (1984).
Nohe et al., Cellular Signalling, 16:291-299 (2004).
Obaru et al., J. Biochem., 99:885 (1986).
Ogawa et al., J. Biol. Chem., 267:14233 (1992).
Ohura et al., J. Biomed. Mat. Res., 30:193-200 (1996).
Ohura et al., J. Biomed. Mat. Res., 44:168-175 (1999).
Okayama et al., Mol. Cell Biol., 2:161-170 (1982).
Ozkaynak et al., EMBO Journal, 9:2085-2093 (1990).
Ozkaynak et al., J. Biol. Chem. 267(35):25220-7 (1992).
Padgett et al., Nature, 325:81-84 (1987).
Paoloni et al., J. Bone Joint Surg., 86A(5):916-22 (2004).
Paralkar, et al., J. Cell Biol., 119:1721-1728 (1992).
Park et al., J. Biol. Chem., 271:8161-9(1996).
Patel et al., Pharmacotherapy of Cognitive Impairment in Alzheimer's Disease: A Review: 81-95 (1992).
Paus, et al., N. Engl. J. Med., 341(7):491-497 (1999).
Perides et al., J. Biol. Chem., 269:765-770 (1994).

Perides et al., PNAS, 89:10326-10330 (1992).
Perry et al., J. Shoulder Elbow Surg., 14:79S-83S (2005).
Peyron, J.G. F. Rheumatol. Suppl., 27:2-3 (1991).
Piek et al., FASEB J., 13:2105-2124 (1999).
Pierce et al., J. Clin. Investig., 96:1336-50 (1995).
Pollock, J. Biol. Chem., 271:8008-14 (1996).
Praemer et al., Musculoskeletal Conditions in the United States, American Academy of Orthopaedic Surgeons, Park Ridge, IL (1992).
Pragnell et al., Blood, 72:196-201 (1998).
2001-2002 Progress Report on Alzheimer's Disease, National Institute on Aging; NIH:1-51 (2002).
Rabin et al., Mol. Cell. Biol., 13:2203-2213 (1993).
Ralph et al., Cancer Res., 37:546 (1977).
Ralph et al., J. Immunol., 114:898 (1975).
Rattner et al., PNAS, 94:2859-2863 (1997).
Razi et al., J. Biol. Chem., 270(19):11267-11275 (1995).
Reddi, A. JBJS, 83-A:S1-1:S1-S6 (2001).
Reddi et al., Osteoporosis, Academic Press, pp. 281-287 (1996).
Reddi et al., PNAS, 69:1601 (1972).
Reeck, Cell, 50:667 (1987).
Rees et al., Biochem J., 350:180-188 (2000).
Riley G., Expert Rev Mol Med., 7(5):1-23 (2005).
Roberts et al., PNAS, 83:4167-4171 (1986).
Robertson et al., Biochem. Biophys. Res. Commun., 149:744-749 (1987).
Rodeo et al., Orthopaedic Res. Soc., 41$^{st}$ Annual Mtg, Orlando, Florida, p. 288 (1995).
Rodeo, et al., J. Bone Joint Surg., 75-A:1795-1803 (1993).
Rolf et al., J. Rheumatol., 24:1595-8 (1997).
Rosen et al., Trends in Genetics, 8:97-102 (1992).
Rosen et al., Connect Tissue Res., 20:313-9 (1989).
Rosen et al., Principles of Bone Biology, 2:919-928 (2002).
Rubin et al., Science, 287:2204-2215 (2000).
Rudinger, Peptide Hormones, Parsons (ed.), U Park Press, Baltimore: 1-7 (1976).
Sakai et al., PNAS, 87:8378-8382 (1990).
Salic et al., Development, 124:4739-4748 (1997).
Sambrook et al., Mol. Cloning: A Laboratory Manual, 2$^{nd}$ Ed., vols. 1,2 and 3, Cold Spring Harbor Laboratory Press: Cold Spring Harbor, New York, USA (1989).
Sampath et al., J. Biol. Chem., 267:20352-20362 (1992).
Sampath et al., J. Biol. Chem., 265:13198-13205 (1990).
Sampath et al., PNAS, 84: 7109-7113 (1987).
Sampath et al., PNAS, 80:6591-6595 (1983).
Sampath et al., Exp. Cell. Res., 143:460-64 (1982).
Sasai et al., Cell, 79:779-790 (1994).
Sato et al., Clin. Orthopaedics Related Res., 183:180-187 (1984).
Sato et al., J. Biol. Chem., 278(5):3063-3071 (2003).
Sato et al., J. Biol. Chem., 278(48):47534-47544 (2003).
Saukkonon et al., J. Exp. Med., 171:439 (1990).
Seeherman et al., J Bone Joint Surg. 85A(Supp. 3):96-108 (2003).
Sen, M., Rheumatology, 44:708-713 (2005).
Schiffelers et al., Arthritis & Rheumatism, 52(4):1314-18 (2005).
Schubert et al., Nature, 344:868-870 (1990).
Schulz et al., Principles of Protein Structure, Springer-Verlag New York, Inc., New York: 14-16 (1979).
Shah, et al., J. Cell Sci., 108:985-1002 (1995).
Shimasaki et al., PNAS, 85:4218-4222 (1988).
Shipley et al., Cancer Res., 46:2068-2071 (1986).
Shoda et al., Growth Factors, 8:165-172 (1993).
Shum et al., Arthritis Res., 4(2):94-106 (2002).
Shworak et al., J. Biol. Chem., 272(44):28008-19 (1997).
Silbert et al., IUBMB Life, 54:177-186 (2002).
Smith et al., Brain Res., 543:111-122 (1991).
Smith et al., Dev. Biol., 138:377-190 (1990).
Smith et al., J. Neurochem., 60:1453-1466 (1993).
Sojar et al., Arch Biochem. Biophys., 259:52-57 (1987).
Sompayrac et al., PNAS, 78:7575-7578 (1981).
Song et al., Mol. Biol. Cell, 5:384a (1994) and 34$^{th}$ Ann. Mtg of the American Soc. for Cell Biol., San Francisco, CA (1994).
Soslowsky et al., J. Shoulder Elbow Surg., 9:79-84 (2000).
Spergel et al., Prog. Neurobiol., 63(6):673-686 (2001).
Sporn et al., Nature, 332:217-219 (1988).
Sporn et al., Science, 233:532-534 (1986).
St-Jaques et al., Current Biol., 8:1058-1068 (1998).
Stein et al., J. Clin. Invest., 108:641-644 (2001).
Stenn et al., Physiol. Rev., 81:449-494 (2001).
Stokes et al., Biochem. J., 360:461-470 (2001).
Storm et al., Nature, 368:639-642 (1994).
Sudo et al., J. Biol. Chem., 279:23134-23141 (2004).
Sugahara et al., IUBMB Life, 54:163-175 (2002).
Sugino et al., J. Biol. Chem., 268:15579 (1993).
Suggs et al., PNAS, 78:6613-6617 (1981).
Sumitomo et al., Biochem. Biophys. Acta., 208:1 (1995).
Sumitomo et al., DNA Sequence-J. DNA Sequence and Mapping 3:297-302 (1993).
Suzuki et al., Proc Natl Acad Sci USA 91:10255-59 (1994).
Sykaras et al., J. Oral Science, 45(2):57-73 (2003).
Tabas et al., Genomics, 9:283-289 (1991).
Takagi et al., Clin. Orthopaed. Related Res., 171:224-231 (1982).
Tallon et al., *Med Sci Sports Exerc* 33(12):1983-90 (2001).
Taniguchi et al., PNAS, 77:5230-5233 (1980).
Tatusova et al., FEMS Microbiol. Lett., 174:247-250 (1990).
Ten Dijke et al., J. Biol. Chem., 269:16985-16988 (1994).
Ten Dijke et al., EMBL Z22534 (Apr. 6, 1993).
Ten Dijke et al., EMBL Sequence Database, European Molecular Biology Laboratory (Basel, CH), Accession No. Z22535 (1993).
Ten Dijke et al., EMBL Sequence Database, European Molecular Biology Laboratory (Basel, CH), Accession No. Z22536 (1993).
Ten Hagen et al., Glycobiology, 13(1):1R-16R (2003).
Thies et al., J. Bone Min. Res., 5:305 (1990).
Thies et al., Endocrinol., 130:1318-1324 (1992).
Thomsen et al., Trends in Genetics, 13:209-211 (1997).
Thomsen et al., Cell, 74:433-441 (1993).
Tona et al., J. Histochem. Cytochem., 41:591-599 (1993).
Toriumi et al., Arch. Otolaryngol. Head Neck Surg., 117:1101-1112 (1991).
Thotakura et al., Meth Enzymol., 138:350-359 (1987).
Tsuchida et al., PNAS, 90:11242-11246 (1993).
Tsukazaki et al., Calcif. Tissue Int., 57:196-200 (1995).
Tuszynski, Cell Transporatation, 9:629-636 (2000).
Ueno et al., PNAS, 84:8282-8286 (1987).
Ulrich et al., EMBO J., 3:361-364 (1984).
Uludag et al., Biotech and Bioengineering 65(6):668-72 (1999).
Urdal et al., PNAS, 81:6481-6485 (1984).
Urist et al., Fed. Proceed., Bethesda, MD, US, 3:746 (1985).
Urist et al., PNAS, 81:371-375 (1984).
Urist et al., Clin. Orthopaed. and Related Res., 187:227-280 (1984).
Urist et al., Proc. Soc. Exper. Biol. & Med., 2:194 (1983).
Urist et al., Science, 220:680-686 (1983).
Urist et al., PNAS, 70:3511 (1973).
Urist et al., Clin. Orthoped. Rel. Res., 214:295-304 (1986).
Urist et al., Science, 150:893-99 (1965).
Urlaub et al., PNAS, 77:4216-20 (1980).
Uyama et al., J. Biol. Chem., 277(11):8841-8846 (2002).
Uyama et al., J. Biol. Chem., 278(5):3072-78 (2003).
Van Mater et al., Genes & Dev., 17:1219-1224(2003).
Vierhapper et al., Metabolism, 52(7):927-929 (2003).
Vukicevic et al., PNAS, 93:9021-6 (1996).
Waard-Van De Spek et al., Clin. and Exp. Dermatology, 14:429-433 (1989).
Wadhwa et al., Current Opinion in Molecular Therapeutics, 6(4):367-372 (2004).
Wahlar et al., Chem. Eur. J., 8(14):3211-3228(2002).
Wall et al., J. Cell Biol., 120:493-502 (1993).
Wang et al., Cell, 67:797-805 (1991).
Wang et al., J. Cell Biochem., Suppl. 15, Part E, p. 161, Abstract Q020 (1991).
Wang et al., PNAS, 87:2220-2224 (1990).
Wang et al., PNAS, 85:9484-9488 (1988).
Wang, E.E., Trends in Biotech., 11:379-383 (1993).
Wang et al., Cell, 88:757-766 (1997).
Wang et al., Stroke, 32:2170-2178 (2001).
Wang et al., J. Biol. Chem. 271:4468-4476 (1996).
Watanabe et al., J. Biochem., 124(4):687-93 (1998).

Weeks et al., Cell, 51:861-867 (1987).
Wells Biochemistry, 29:8509-8517 (1990).
Wharton et al., PNAS, 88:9214-9218 (1991).
White et al., J. Biol. Chem., 270(41):24156-65 (1995).
Winkler et al., J. Biol. Chem., 279(35):36293-36298 (2004).
Wissmann et al., J. Pathol., 201:204-212 (2003).
Wolfman et al., J. Clin. Invest., (100)2:321-330 (1997).
Wolpe et al., FASEB J., 3:2565-2573 (1989).
Wolpe et al., J. Biochem. Supple. O, Abstract H141, 13 Part C:21 (1989).
Wolpe et al., J. Exp. Mad., 167:570 (1988).
Wong et al., Science, 228:810-815 (1985).
Woo et al., PNAS, 75:3688-3691 (1978).
Wood et al., PNAS. 82:1585-1588 (1985).
Woodwell et al., Adv. Data, 346:1-44 (2004).
Wozney et al., J. Cell Sci., Supple. 13:149-156 (1990).
Wozney, Mol. Reproduction & Develop., 32:160-167 (1992).
Wozney et al., Science, 242:1528-1534 (1988).
Wozney, J.M., Prog. Growth Factor Res. 1:267-280 (1989).
Wozney et al., Handbook of Exp. Pharm., eds., G.R. Mundy and T.J. Martin: Springer-Verlag, Berlin, Chapter 20, 107:725-748 (1993).
Wozney, Cell. & Mol. Biol. Bone, pp. 131-167 (1993) (Academic Press, Inc.).
Wozney et al., J. Cell Biochem., Suppl. 16F:76 Abstract (1992).
Wozney Spine, 27:S2-S8 (2002).
Wright et al., Leukemia Res., 4:537 (1980).
Wright et al., Cell Tissue Kinet., 18:193 (1985).
Xu et al., Proc Natl Acad Sci USA, 91:7957-61 (1994).
Yamaguchi et al., Nippon Rinsho, 50:1932-1938 (1992).
Yamaji et al., Biochem. Biophys. Res. Comm., 205:1944-1951 (1994).
Zamore et al., Nat. Struct. Biol., 8(9):746-750 (2001).
Zipfel et al., J. Immunol., 142:1582 (1989).
Zheng et al., Path. Res., Pract., 188:1104-1121 (1992).
Zhou et al., Nature, 361:543-547 (1993).

* cited by examiner

SEQUENCE LISTING

<160> NUMBER OF SEQ ID NOS: 7

<210> SEQ ID NO 1
<211> LENGTH: 21
<212> TYPE: DNA
<213> ORGANISM: cytomegalovirus

<400> SEQUENCE: 1
tggatgttgc ctttacttct a                                              21

<210> SEQ ID NO 2
<211> LENGTH: 20
<212> TYPE: DNA
<213> ORGANISM: Simian virus 40

<400> SEQUENCE: 2
ttcactgcat tctagttgtg                                                20

<210> SEQ ID NO 3
<211> LENGTH: 20
<212> TYPE: DNA
<213> ORGANISM: Homo sapiens

<400> SEQUENCE: 3
tgtgaacctg gtggagtacg                                                20

<210> SEQ ID NO 4
<211> LENGTH: 22
<212> TYPE: DNA
<213> ORGANISM: Homo sapiens

<400> SEQUENCE: 4
aagaaccgag atggcattta gc                                             22

<210> SEQ ID NO 5
<211> LENGTH: 29
<212> TYPE: DNA
<213> ORGANISM: Simian virus 40

<400> SEQUENCE: 5
gacatgataa gatacattga tgagtttgg                                      29

<210> SEQ ID NO 6
<211> LENGTH: 26
<212> TYPE: DNA
<213> ORGANISM: Simian virus 40

<400> SEQUENCE: 6
gcaatagcat cacaaatttc acaaat                                         26

<210> SEQ ID NO 7
<211> LENGTH: 35
<212> TYPE: DNA
<213> ORGANISM: Simian virus 40

<400> SEQUENCE: 7
caaaccacaa ctagaatgca gtgaaaaaaa tgctt                               35

COMPOSITIONS AND METHODS FOR SYSTEMIC ADMINISTRATION OF SEQUENCES ENCODING BONE MORPHOGENETIC PROTEINS

CONTINUING APPLICATION DATA

This application claims priority from U.S. provisional application Ser. No. 60/295,153, filed Jun. 1, 2001.

BACKGROUND OF THE INVENTION

The present invention relates to the field of tissue repair. More particularly, the present invention relates to compositions and methods for systemic administration of sequences encoding osteogenic proteins. The invention also includes methods and compositions for the systemic administration of osteogenic proteins for promotion of osteogenesis. The compositions and methods promote osteogenesis and therefore uses include fracture healing and repair and acceleration of fracture healing. These methods and compositions may also be used for the treatment of osteoporotic bone and or the prevention and treatment of osteoporosis.

SUMMARY OF THE INVENTION

The present invention is directed to compositions and methods for systemic administration of DNA sequences encoding osteogenic proteins. The invention also includes methods and compositions for the systemic administration of osteogenic proteins or peptides for promotion of osteogenesis. The compositions and methods may be used to promote fracture healing and repair and acceleration of fracture healing. These methods and compositions may also be used for the treatment of osteoporotic or osteopenic bone and or the prevention and treatment of osteoporosis.

The osteogenic proteins and DNA sequences encoding them are preferably selected from the family of proteins known as the transforming growth factors-beta (TGF-β) superfamily of proteins, which includes the bone morphogenetic proteins (BMPs), activins and inhibins. Most preferably, the active agent includes at least one DNA sequence encoding protein selected from the subclass of proteins known generally as BMPs, which have been disclosed to have osteogenic activity, and other growth and differentiation type activities. These BMPs include BMP proteins BMP-2, BMP-3, BMP-4, BMP-5, and BMP-7, BMP-10, BMP-12 and BMP-13, BMP-15, BMP-16, further described below. The osteogenic agent is most preferably the DNA sequences encoding BMP-6 or BMP-6 proteins or peptides. The DNA and protein sequence and methods for producing BMP-6 are disclosed in U.S. Pat. Nos. 5,187,076, 5,459,047 and 5,849,880 and in U.S. Ser. No. 09/189,157, the disclosures of which are herein incorporated by reference. Other agents and the DNA sequences encoding them which are capable of inducing bone growth or fracture repair or increasing the formation of bone tissue may also be utilized.

The invention therefore provides compositions and methods for promoting osteogenesis wherein the composition comprises a DNA sequence encoding an osteogenic protein in an injectable formulation suitable for systemic administration. In preferred embodiments the osteogenic protein is a bone morphogenetic protein (BMP). Such compositions are useful for fracture healing and repair. These compositions may be used for increasing bone mineral density. Osteoporotic or osteopenic bone is often characterized by suboptimal bone density and therefore the compositions and methods may be used for increasing bone mineral density and treating osteoporosis.

In a preferred embodiment, the invention features a composition and method for promoting fracture repair wherein the composition comprises a DNA sequence encoding BMP-6 and is employed in a method involving systemic administration to a patient in need of fracture repair. The DNA and protein sequence and methods for producing BMP-6 are disclosed in U.S. Pat. Nos. 5,187,076, 5,459,047 and 5,849,880 and in 6,207,813, the disclosures of which are herein incorporated by reference. In other embodiments the following BMPs may be suitable: BMP-2, BMP-3, BMP-4, BMP-5, BMP-7, BMP-10, BMP-12 and BMP-13, BMP-15, and BMP-16, further described below.

In the present invention, the vectors used for incorporation and expression of the DNA are preferably viral in origin, particularly adenoviruses, as well as retroviruses. Adenoviruses are advantageous in that they do not require cells in the state of proliferation, and have a high efficiency rate of infection both in vitro and in vivo, whereas retroviruses are more often suitable for in vitro infection. Adenoviruses also offer high levels of transgene expression and the ability to achieve high titers. These advantages make adenoviruses more suitable for primary cells, cell lines and direct in vivo transduction. In addition, expression of the transgene is transient and the adenoviral vector does not integrate into the cell genome, making the vectors safer for use. All generations of recombinant adenoviruses are suitable, including the present generation, (E1 deleted), and new generations which have reduced antigenicity (E1, E3, E4 deleted viruses, or E1, E4 deleted and E3 overexpressed). Smith (1995); Dunbar (1996); Roemer (1992); Graham (1991); Kozarsky (1993); and Ilan (1997). The disclosure of each of the above publications is hereby incorporated by reference for the contents thereof.

The expression of the genes which are expressed in the present invention may be constitutive or controlled. Controlling the expression can be achieved by external control by means of regulatory elements, such as with an inducibly controlled promoter, for example, a tetracycline controlled promoter, as further described herein, or by using regulatory elements from tissue specific or temporally specific genes to direct the expression only to certain specified differentiation pathways or at certain stages in differentiation. For example, the osteocalcin promoter may be used for induction at late stages of bone formation and calcification.

In a preferred embodiment the BMP DNA sequence, preferably BMP-6 is contained on an adenovirus vector comprising an injectable formulation suitable for systemic administration. This composition may be used in a method comprising systemic administration a therapeutically effective amount of the composition to a patient in need of fracture repair.

The invention further provides methods and compositions for promoting osteogenesis wherein the composition comprises an osteogenic protein. In preferred embodiments the osteogenic protein is a bone morphogenetic protein (BMP). Such compositions are useful for fracture healing and repair. These compositions may be used for increasing bone mineral density. Osteoporotic or osteopenic bone is often characterized by suboptimal bone density and therefore the compositions and methods may be used for for increasing bone mineral density and treating osteoporosis.

In a preferred embodiment, the invention features a composition and method for promoting fracture repair wherein the composition comprises BMP-6 and is employed in a method involving systemic administration to a patient in need of fracture repair.

In other embodiments the following BMPs may be suitable: BMP-2, BMP-3, BMP-4, BMP-5, BMP-7, BMP-10, BMP-12 and BMP-13, BMP-15, and BMP-16, further described below.

In preferred embodiments, the active agent is one or more proteins selected from the group of proteins known as the Transforming Growth Factors-Beta (TGF-β) superfamily of proteins, preferably selected from the Bone Morphogenetic Proteins (BMPs), the Growth and Differentiation Factors (GDFs), as well as other proteins, as described more fully herein. Osteogenic proteins, DNA sequences, compositions and methods for producing them, useful in the present invention, are those comprising the BMP proteins BMP-2, BMP-3, BMP-4, BMP-5, BMP-6 and BMP-7, disclosed for instance in U.S. Pat. Nos. 5,108,922; 5,013,649; 5,116,738; 5,106,748; 5,187,076, 5,459,047, 5,849,880; and 5,141,905; BMP-8, disclosed in PCT publication WO91/18098; and BMP-9, disclosed in PCT publication WO93/00432, BMP-10, disclosed in PCT application WO94/26893; BMP-11, disclosed in PCT application WO94/26892, or BMP-12 or BMP-13, disclosed in PCT application WO95/16035, or BMP-15, disclosed in PCT application WO96/36710 or BMP-16, disclosed in U.S. Pat. No. 5,965,403.

Other DNA molecules and the proteins which they encode which may also be useful include those encoding Vgr-2, and any of the growth and differentiation factors [GDFs], including those described in PCT applications WO94/15965; WO94/15949; WO95/01801; WO95/01802; WO94/21681; WO94/15966; and others. Also useful in the present invention may be BIP, disclosed in WO94/01557; and MP52, disclosed in PCT application WO93/16099. The disclosures of all of the above applications are hereby incorporated by reference for the disclosure contained therein.

Other DNA molecules and the proteins which they encode which may be useful, in addition to DNA encoding a BMP protein, include DNA molecules encoding other therapeutically useful agents including growth factors such as epidermal growth factor (EGF), fibroblast growth factor (FGF), transforming growth factor (TGF-α and TGF-β), hedgehog proteins such as sonic, indian and desert hedgehog, parathyroid hormone and parathyroid hormone related peptide, cadherins, activins, inhibins, and IGF, FSH, frizzled, frzb or frazzled proteins, PDGF and other endothelial growth factors, BMP binding proteins such as chordin and fetuin, estrogen and other steroids as well as truncated versions thereof, and transcription factors such as wnt proteins, mad genes and cbfa.

The disclosures of the above identified applications are hereby incorporated herein by reference. The unique inductive activities of these proteins, along with their presence in bone, suggests that they are important regulators of bone and cartilage repair processes, and may be involved in the normal maintenance of bone tissue.

DETAILED DESCRIPTION OF THE INVENTION

Figure 1:
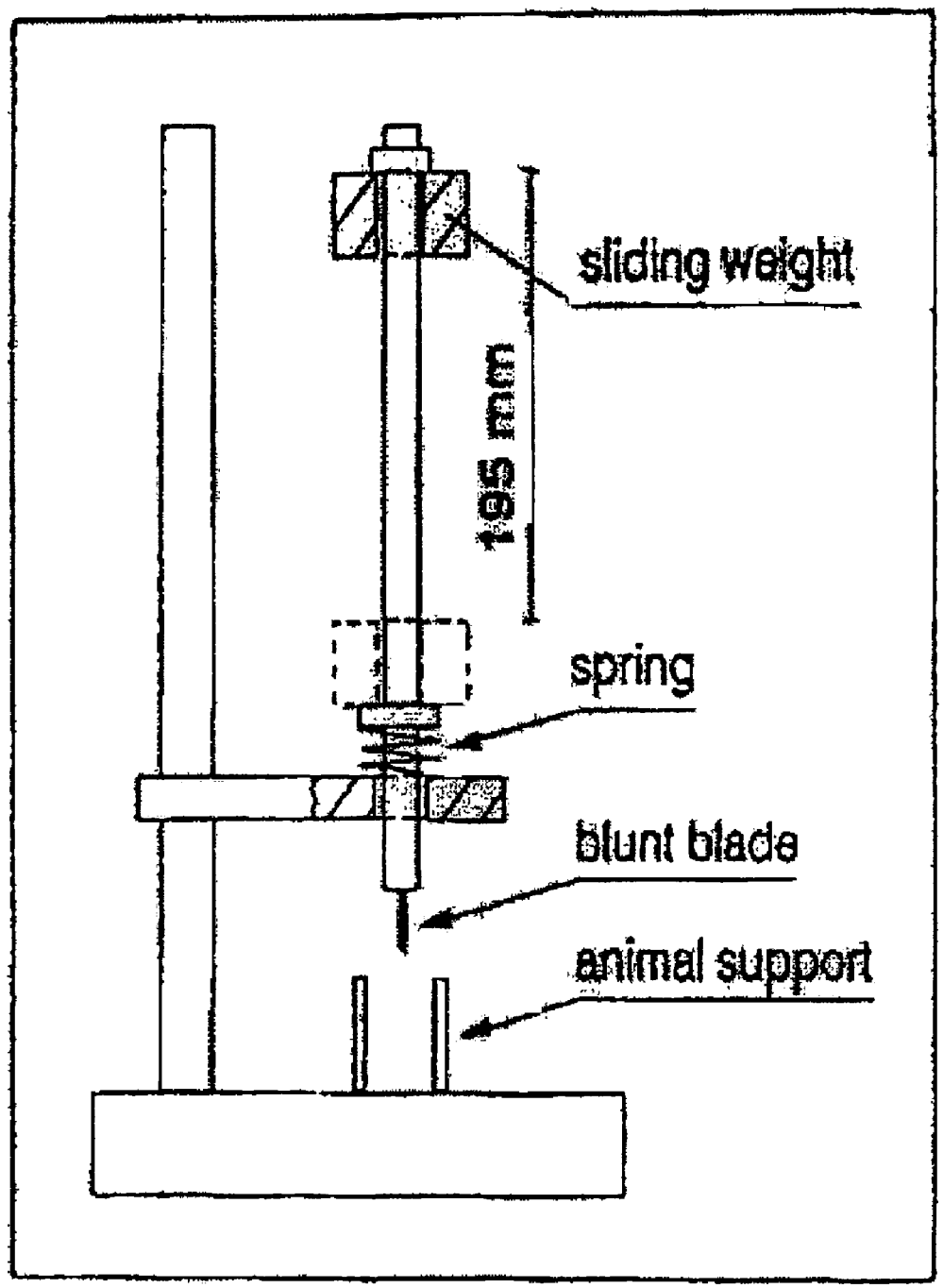
FIG. 1 is an illustration of the fracture apparatus utilized in the closed-femur fracture model.

The invention provides compositions and methods for promoting osteogenesis. The compositions of the invention comprise a DNA sequence encoding an osteogenic protein in an injectable formulation suitable for systemic administration. In preferred embodiments the osteogenic protein is a bone morphogenetic protein (BMP). Such compositions are useful for fracture healing and repair. These compositions may be used for increasing bone mineral density. Osteoporotic or osteopenic bone is often characterized by suboptimal bone density and therefore the compositions and methods may be used for for increasing bone mineral density and treating osteoporosis.

In a preferred embodiment, the invention features a composition and method for promoting fracture repair wherein the composition comprises a DNA sequence encoding BMP-6 and is employed in a method involving systemic administration to a patient in need of fracture repair. The DNA and protein sequence and methods for producing BMP-6 are disclosed in U.S. Pat. Nos. 5,187,076, 5,459,047 and 5,849,880 and in 6,207,813, the disclosures of which are herein incorporated by reference. In a further preferred embodiment the BMP DNA sequence is contained on an adenovirus vector.

In other embodiments the following BMPs may be suitable: BMP-2, BMP-3, BMP-4, BMP-5, BMP-6 and BMP-7, BMP-9, BMP-10, BMP-12 and BMP-13, BMP-15, BMP-16, further described herein.

The invention further provides methods and compositions for promoting osteogenesis wherein the composition comprises an osteogenic protein. These proteins may be chemically modified to provide an injectable formulation suitable for systemic administration. Such modification is known to those skilled in the art. In preferred embodiments the osteogenic protein is a bone morphogenetic protein (BMP) suitable for systemic administration. Such compositions are useful for fracture healing and repair. These compositions may be used for increasing bone mineral density. Osteoporotic or osteopenic bone is often characterized by suboptimal bone density and therefore the compositions and methods may be used for for increasing bone mineral density and treating osteoporosis.

In a preferred embodiment, the invention features a composition and method for promoting fracture repair wherein the composition comprises BMP-6, described above, and is employed in a method involving systemic administration to a patient in need of fracture repair.

In other embodiments the following BMPs may be suitable: BMP-2, BMP-3, BMP-4, BMP-5, BMP-7, BMP-9, BMP-10, BMP-12 and BMP-13, BMP-15, BMP-16, further described below.

The invention therefore provides compositions and methods for promoting osteogenesis wherein the composition comprises a DNA sequence encoding an osteogenic protein. In preferred embodiments the osteogenic protein is a bone morphogenetic protein (BMP). Such compositions are useful for fracture healing and repair. These compositions may be used for increasing bone mineral density. Osteoporotic or osteopenic bone is often characterized by suboptimal bone density and therefore the compositions and methods may be used for for increasing bone mineral density and treating osteoporosis. The methods and compositions may increase bone mass density and minimize or reduce the incidence of osteoporosis-related fractures. The methods comprise administering an injectable formulation of a DNA sequence encoding an osteogenic protein suitable for systemic administration in an amount effective for fracture repair. The compositions may be administered in admixture with a pharmaceutically acceptable vehicle.

In a preferred embodiment, the invention features a composition and method for promoting fracture repair wherein the composition comprises a DNA sequence encoding BMP-6 and is employed in a method involving systemic administration to a patient in need of fracture repair. In a further preferred embodiment the BMP DNA sequence is contained on an adenovirus vector.

In other embodiments the following BMPs may be suitable: BMP-2, BMP-3, BMP-4, BMP-5, BMP-6 and BMP-7, BMP-10, BMP-12 and BMP-13, BMP-15, BMP-16, further described below.

The invention further provides methods and compositions for promoting osteogenesis wherein the composition comprises an osteogenic protein. In preferred embodiments the osteogenic protein is a bone morphogenetic protein (BMP). Such compositions are useful for fracture healing and repair. These compositions may be used for increasing bone mineral density. Osteoporotic or osteopenic bone is often characterized by suboptimal bone density and therefore the compositions and methods may be used for for increasing bone mineral density and treating osteoporosis. The composition and method therefore as an injectable agent would be useful in fracture prevention and treatment without surgical intervention. The composition and method would decrease the occurance and/or severity of fracture to osteoporotic bone.

In a preferred embodiment, the invention features a composition and method for promoting fracture repair wherein the composition comprises BMP-6 and is employed in a method involving systemic administration to a patient in need of fracture repair.

In other embodiments the following BMPs may be suitable: BMP-2, BMP-3, BMP-4, BMP-5, BMP-6 and BMP-7, BMP-10, BMP-12 and BMP-13, BMP-15, BMP-16, further described below.

The sequences encoding osteogenic proteins as well as the proteins are preferably selected from the family of proteins known as the transforming growth factors-beta (TGF-β) superfamily of proteins, which includes the bone morphogenetic proteins (BMPs), activins and inhibins. Most preferably, the active agent includes at least one protein selected from the subclass of proteins known generally as BMPs, which have been disclosed to have osteogenic activity, and other growth and differentiation type activities. These BMPs include BMP proteins BMP-2, BMP-3, BMP-4, BMP-5, and BMP-7, BMP-10, BMP-12 and BMP-13, BMP-15, BMP-16, further described below. The osteogenic agent is most preferably the DNA sequences encoding BMP-6 or BMP-6 proteins or peptides. The DNA and protein sequence and methods for producing BMP-6 are disclosed in U.S. Pat. Nos. 5,187,076, 5,459,047 and 5,849,880 and in 6,207,813, the disclosures of which are herein incorporated by reference. Other agents and the DNA sequences encoding them which are capable of inducing bone growth or fracture repair or increasing the formation of bone tissue may also be utilized.

Among the DNA molecules and proteins useful in the present invention are those comprising the coding sequences for one or more of the BMP proteins BMP-2, BMP-3, BMP-4, BMP-5, BMP-6 and BMP-7, disclosed for instance in U.S. Pat. Nos. 5,108,922; 5,013,649; 5,116,738; 5,106,748; 5,187,076; and 5,141,905; BMP-8, disclosed in PCT publication WO91/18098; and BMP-9, disclosed in PCT publication WO93/00432, BMP-10, disclosed in PCT application WO94/26893; BMP-11, disclosed in PCT application WO94/26892, or BMP-12 or BMP-13, disclosed in PCT application WO95/16035, or BMP-15, disclosed in PCT application WO96/36710 or BMP-16, disclosed in U.S. Pat. No. 5,965,403.

Other DNA molecules which may also be useful include those encoding Vgr-2, and any of the growth and differentiation factors [GDFs], including those described in PCT applications WO94/15965; WO94/15949; WO95/01801; WO95/01802; WO94/21681; WO94/15966; and others. Also useful in the present invention may be BIP, disclosed in WO94/01557; and MP52, disclosed in PCT application WO93/16099. The disclosures of all of the above applications are hereby incorporated by reference for the disclosure contained therein.

Other DNA molecules which may be useful, in addition to DNA encoding a BMP protein, include DNA molecules encoding other therapeutically useful agents including growth factors such as epidermal growth factor (EGF), fibroblast growth factor (FGF), transforming growth factor (TGF-α and TGF-β), hedgehog proteins such as sonic, indian and desert hedgehog, parathyroid hormone and parathyroid hormone related peptide, cadherins, activins, inhibins, and IGF, FSH, frizzled, frzb or frazzled proteins, PDGF and other endothelial growth factors, BMP binding proteins such as chordin and fetuin, estrogen and other steroids as well as truncated versions thereof, and transcription factors such as wnt proteins, mad genes and cbfa.

In the present invention, the vectors used for incorporation and expression of the DNA are preferably viral in origin, particularly adenoviruses, as well as retroviruses. Adenoviruses are advantageous in that they do not require cells in the state of proliferation, and have a high efficiency rate of infection both in vitro and in vivo, whereas retroviruses are more often suitable for in vitro infection. Adenoviruses also offer high levels of transgene expression and the ability to achieve high titers. These advantages make adenoviruses more suitable for primary cells, cell lines and direct in vivo transduction. In addition, expression of the transgene is transient and the adenoviral vector does not integrate into the cell genome, making the vectors safer for use. All generations of recombinant adenoviruses are suitable, including the present generation, (E1 deleted), and new generations which have reduced antigenicity (E1, E3, E4 deleted viruses, or E1, E4 deleted and E3 overexpressed). Smith (1995); Dunbar (1996); Roemer (1992); Graham (1991); Kozarsky (1993); and Ilan (1997). The disclosure of each of the above publications is hereby incorporated by reference for the contents thereof.

The expression of the genes which are expressed in the present invention may be constitutive or controlled. Controlling the expression can be achieved by external control by means of regulatory elements, such as with an inducibly controlled promoter, for example, a tetracycline controlled promoter, as further described herein, or by using regulatory elements from tissue specific or temporally specific genes to direct the expression only to certain specified differentiation pathways or at certain stages in differentiation. For example, the osteocalcin promoter may be used for induction at late stages of bone formation and calcification.

The DNA sequences encoding BMP proteins useful in the present invention, as disclosed in the referenced applications and patents cited above, also include the disclosed DNA sequences, free of association with DNA sequences encoding other proteinaceous materials, and coding on expression for the proteins of the invention. These DNA sequences include those depicted in Tables II and III in a 5' to 3' direction or portions thereof. Further included are those sequences which hybridize under stringent hybridization conditions [see, T. Maniatis et al, *Molecular Cloning (A Laboratory Manual)*, Cold Spring Harbor Laboratory (1982), pages 387 to 389] to the particular DNA sequence and demonstrate cartilage and/or bone formation activity. Such cartilage and/or bone formation activity may be in the rat bone formation assay. An example of one such stringent hybridization condition is hybridization at 4×SSC at 65° C., followed by a washing in 0.1×SCC at 65° C. for an hour. Alternatively, an exemplary stringent hybridization condition is in 50% formamide, 4×SCC at 42° C.

Similarly, DNA sequences which encode proteins similar to the protein encoded by the disclosed sequence, but which differ in codon sequence due to the degeneracies of the genetic code or allelic variations (naturally-occurring base changes in the species population which may or may not result in an amino acid change) also encode the proteins of the invention described herein. Variations in the DNA sequences which are caused by point mutations or by induced modifications (including insertion, deletion, and substitution) to enhance the activity, half-life or production of the polypeptides encoded thereby are also encompassed in the invention.

Similarly, the proteins provided herein also include factors encoded by the sequences similar to those of naturally-occurring BMP related proteins, such as BMP-6, but into which modifications are naturally provided (e.g. allelic variations in the nucleotide sequence which may result in amino acid changes in the polypeptide) or deliberately engineered. For example, synthetic polypeptides may wholly or partially duplicate continuous sequences of the amino acid residues of the particular BMP. These sequences, by virtue of sharing primary, secondary, or tertiary structural and conformational characteristics with bone inductive polypeptides of naturally-occurring BMP s may possess biological properties in common therewith.

In further embodiments, compositions and methods of the present invention may comprise, in addition to the DNA sequences encoding, for example a BMP protein, A DNA sequence encoding additional proteins, such as additional members of the TGF-β superfamily of proteins, described above.

These compositions and methods may be used to promote osteogenesis and in fracture repair. The compositions and methods may also be useful in increasing bone mass density.

In one embodiment of the invention, wherein it is the protein which is systemically administered such protein can be modified for systemic administration. Such modification can include chemical modification by procedures and methods known to those skilled in the art.

In another embodiment the protein can be modified or otherwise formulated for controlled release. In such a composition, the BMP protein is preferably encapsulated, or otherwise administered in a manner which allows for example, slow release over a sustained period of time. For example, the BMP component may be encapsulated in a resorbable polymer delivery system, such as polylactic acid, polyglycolic acid or copolymers thereof, polyorthoesters, polyorthocarbonates, and other polymers. Suitable polymers are disclosed for example in EP 0145240, the disclosure of which is hereby incorporated by reference.

It is expected that osteogenic proteins may act in concert with or perhaps synergistically with other related proteins and growth factors. Therefore, further therapeutic methods and compositions of the invention therefore comprise a therapeutic amount of a sequence encoding an osteogenic protein or an osteogenic protein or peptide with a therapeutic amount of at least one of the BMP proteins described above.

Such compositions may comprise separate molecules of the BMP proteins or heteromolecules comprised of different BMP moieties.

Compositions and methods of the present invention may be combined with other agents beneficial to the treatment of the defect, wound, or tissue in question.

In the present invention, the vectors used for incorporation and expression of the DNA are preferably viral in origin, particularly adenoviruses, as well as retroviruses. Adenoviruses are advantageous in that they do not require cells in the state of proliferation, and have a high efficiency rate of infection both in vitro and in vivo, whereas retroviruses are more often suitable for in vitro infection. Adenoviruses also offer high levels of transgene expression and the ability to achieve high titers. These advantages make adenoviruses more suitable for primary cells, cell lines and direct in vivo transduction. In addition, expression of the transgene is transient and the adenoviral vector does not integrate into the cell genome, making the vectors safer for use. All generations of recombinant adenoviruses are suitable, including the present generation, (E1 deleted), and new generations which have reduced antigenicity (E1, E3, E4 deleted viruses, or E1, E4 deleted and E3 overexpressed). Smith (1995); Dunbar (1996); Roemer (1992); Graham (1991); Kozarsky (1993); and Ilan (1997). The disclosure of each of the above publications is hereby incorporated by reference for the contents thereof.

The expression of the genes which are expressed in the present invention may be constitutive or controlled. Controlling the expression can be achieved by external control by means of regulatory elements, such as with an inducibly controlled promoter, for example, a tetracycline controlled promoter, as further described herein, or by using regulatory elements from tissue specific or temporally specific genes to direct the expression only to certain specified differentiation pathways or at certain stages in differentiation. For example, the osteocalcin promoter may be used for induction at late stages of bone formation and calcification.

The therapeutic method includes administering the composition systemically as an injectable. In certain embodiments the method involves local injection. The composition may further involve an implant or device. When administered, the therapeutic composition for use in this invention is, of course, in a pyrogen-free, physiologically acceptable form. Further, the composition may desirably be encapsulated or injected in a viscous form for delivery to the site of tissue damage. Therapeutically useful agents which may also optionally be included in the composition as described above, may alternatively or additionally, be administered simultaneously or sequentially with the composition in the methods of the invention. In addition, the compositions of the present invention may be used in conjunction with presently available treatments.

In embodiments for example for treatment of osteoporotic conditions, materials which may be useful as the carrier in practicing the present invention include pharmaceutically acceptable materials having viscosity and polarity such that, when added to the bone morphogenetic protein, form a composition that possesses appropriate handling characteristics for injectable application to the site of osteoporotic or osteopenic bone. Adding the carrier to the bone morphogenetic protein allows the protein to remain in the diseased or lesioned site for a time sufficient to allow the protein to increase the otherwise natural rate of regenerative osteogenic activity of the infiltrating mammalian progenitor or other cells, and to form a space in which new tissue can grow and allow for ingrowth of cells. The carrier may also allow the bone morphogenetic protein to be released from the disease or lesion site over a time interval appropriate for optimally increasing the rate of regenerative osteogenic activity of the progenitor cells. The carrier may also supply a framework on which to induce new formation in severely osteoporotic bone.

The most preferred family of carriers comprises collagenous materials. These are preferably in a form suitable for injection, such as a gel. Such gels may be cross-linked or non-cross-linked. Other forms of collagen, such as dispersions or fibrillar collagen, may also be useful in the methods of the present invention. Another preferred family of carriers is cellulosic materials such as alkylcellulose, including hydroxyalkylcellulose, methylcellulose, ethylcellulose, hydroxyethylcellulose, hydroxypropylcellulose, hydroxypropylmethylcellulose, and carboxymethylcellulose, the most preferred being the cationic salts of carboxymethylcellulose (CMC).

In the case of cellulosic carriers and collagen gels, it is preferred that the carrier be in the form of a hydrated cellulosic viscous gel. Viscosity may be increased through mechanical means, such as high agitation for a suitable period of time, followed by autoclaving, or chemically. The active agent and cellulosic carrier is preferably in a solution of suitable buffer. One preferred buffer solution is a composition comprising, in addition to the active agent, about 1.0 to about 10.0% (w/v) glycine, about 0.1 to about 5.0% (w/v) of a sugar, preferably sucrose, about 1 to about 20 mM glutamic acid hydrochloride, and optionally about 0.01 to about 0.1% of a non-ionic surfactant, such as polysorbate 80. Preferred solutions are from about 1% to about 20% w/v cellulosic carrier/buffer. If desired, a salt may be added. A preferred viscous gel carrier is described in Example 2 below. The amount of osteogenic protein useful with viscous gel carrier is generally in a range of from about 0.1 to about 100 mg, preferably about 1 to about 100 mg; most preferably about 10 to about 80 mg per cubic centimeter of implant material required.

Another class of materials of particular interest for injectable carriers are resorbable hydroxyapatites as well as minerals, ceramics and phosphates. Resorbable hydroxyapatites, for example, can be formulated at various porosities with varying resorption rates; their handling characteristics vary from hard implantable types, to gel-like consistency, to those that are injectable but harden at body temperature. Suitable hydroxyapatite and ceramic carriers are described, for example in WO96/36562; and U.S. Pat. Nos. 5,543,019; 5,306,305; 5,258,044; 5,496,399; 5,455,231; 5,336,264; 5,178,845; 5,053,212; 5,047,031; 5,129,905; 5,034,059; 4,880,610; 5,290,763; and 5,563,124; the disclosures of which are incorporated herein by reference.

Another preferred family of carriers for administration of the active agent of the present invention are injectable polymers, which may be viscous and which may optionally include a sequestering agent as well. Suitable polymers and sequestering agents include those described in U.S. Pat. No. 5,171,579, the entire disclosure of which is incorporated herein by reference. Other polymers include the pluronics, such as Poloxamer 407 gel. Pluronics are a class of water soluble ABA type block surfactant copolymers which exhibit the unique property of reverse thermal gelation. They are liquid (and hence syringeable) at 4° C. and gel at body temperature. Poloxamer 407, MW 12,500, is excreted unchanged in the urine after systemic absorption and has supposedly been shown to be non-toxic in animals. Polylactides and/or polyethylene glycols, including poly(lactide)/poly(ethylene glycol)gels. Polylactides may be dissolved in polyethylene glycols, such as low molecular weight (2000) PLA dissolved in PEG to produce a syringeable solution that precipitates PLA upon injection into an aqueous environment, resulting in a relatively firm gel. In addition, the literature cites conjugates, such as Poly(lactic acid)-poly(ethylene glycol)conjugates, as appropriate carriers for BMPs (Miyamoto et al., Clin. Orthop. Rel. Res. 294:333 (1993)). Among the materials useful as sequestering agents are hyaluronic acid, sodium alginate, poly(ethylene glycol), polyoxyethylene oxide, carboxyvinyl polymer and poly(vinyl alcohol), and cellulosic materials, such as hydroxycelluloses. One such preferred agent is carboxymethylcellulose.

The above materials disclosed to be useful as sequestering agents may themselves be useful as carriers for injection. In addition, combinations of the above described materials may be used.

In cases where the carrier may be of higher viscosity than optimal, the carrier may optionally be combined with a diluent, such as aqueous glycerol, preferably the carrier diluent would be present in concentrations of about 10 to about 80% (v/v). Also, the above materials may be combined in particular embodiments of the present invention. For example, polymers, such as porous particulate polymers, may be dissolved or suspended in cellulosic or gel carriers to increase viscosity.

In a preferred embodiment of the present invention, the active agents are administered locally through injection using only a suitable buffer as carrier. One suitable buffer comprises glycine, sucrose, and glutamic acid hydrochloride, at a pH of less than 6.0. Preferred compositions of buffer solutions comprise about 1.0 to about 10.0% (w/v) glycine, about 0.1 to about 5.0% (w/v) of a sugar, preferably sucrose, about 1 to about 20 mM glutamine, glutamic acid, or glutamic acid hydrochloride, and optionally about 0.01 to about 0.1% of a non-ionic surfactant, such as polysorbate 80. In a preferred embodiment of the invention, this formulation comprises about 2.5% glycine (g/100 ml (w/v)), about 0.5% sucrose (w/v), about 5 mM glutamic acid hydrochloride (about 0.1% w/v), and about 0.01% (w/v) polysorbate 80, at a pH of about 4.5. This buffer has been described as MFR 842. Further buffers suitable for use in the present invention are described in U.S. Pat. No. 5,385,887, the disclosure of which is hereby incorporated by reference. Preferred solutions may also include combinations of buffer and other carrier, such as a combination of buffer and cellulosic carrier. Preferred ranges for this combination are from about 1% to about 20% w/v cellulosic carrier/buffer. If desired, a salt may be added.

In certain embodiments, the compositions may include an appropriate matrix and/or sequestering agent as a carrier. For instance, the matrix may support the composition or provide a surface for cartilaginous and/or bone tissue formation and/or other tissue formation. The matrix may provide slow release of the protein and/or the appropriate environment for presentation thereof. The sequestering agent may be a substance which aids in ease of administration through injection or other means, or may slow the migration of protein from the site of application.

In some embodiments, genetically engineered cells may be administered in combination with an appropriate matrix, for instance, for supporting the composition and providing a surface for bone, cartilage, and/or other connective tissue growth. The matrix may be in the form of traditional matrix biomaterials. The matrix may provide slow release of the expressed protein and differentiated cells and/or the appropriate environment for presentation thereof. In some embodiments, various collagenous and non-collagenous proteins are expected to be upregulated and secreted from the pluripotent stem cells. This phenomenon accelerates tissue regeneration by enhancing matrix deposition. Matrix proteins can also be expressed in the genetically engineered cells and enhance the engraftment and attachment of transplanted cells into the transplant area.

The choice of a carrier material is based on biocompatibility, biodegradability, mechanical properties, cosmetic appearance and interface properties. The particular application of the compositions will define the appropriate formulation. Potential matrices for the compositions may be biodegradable and chemically defined. Further matrices are comprised of pure proteins or extracellular matrix components. Other potential matrices are non-biodegradable and chemically defined. Preferred matrices include collagen-based materials, including sponges, such as Helistat[7] (Integra LifeSciences, Plainsboro, N.J.), or collagen in an injectable form, as well as sequestering agents, which may be biodegradable, for example hyaluronic acid derived. Biodegradable materials, such as cellulose films, or surgical meshes, may also serve as matrices. Such materials could be sutured into an injury site, or wrapped around the cartilage.

Another preferred class of carrier are polymeric matrices, including polymers of poly(lactic acid), poly(glycolic acid) and copolymers of lactic acid and glycolic acid. These matrices may be in the form of a sponge, or in the form of porous particles, and may also include a sequestering agent. Suitable polymer matrices are described, for example, in WO93/00050, the disclosure of which is incorporated herein by reference.

Preferred families of sequestering agents include blood, fibrin clot and/or cellulosic materials such as alkylcelluloses (including hydroxyalkylcelluloses), including methylcellulose, ethylcellulose, hydroxyethylcellulose, hydroxypropylcellulose, hydroxypropyl-methylcellulose, and carboxymethylcellulose, the most preferred being cationic salts of carboxymethylcellulose (CMC). Other preferred sequestering agents include hyaluronic acid, sodium alginate, poly (ethylene glycol), polyoxyethylene oxide, carboxyvinyl polymer and poly(vinyl alcohol). The amount of sequestering agent useful herein is 0.5–20 wt %, preferably 1–10 wt % based on total formulation weight, which represents the amount necessary to prevent desorbtion of the protein from the polymer matrix and to provide appropriate handling of the composition, yet not so much that the progenitor cells are prevented from infiltrating the matrix, thereby providing the protein the opportunity to assist the activity of the progenitor cells.

Additional optional components useful in the practice of the subject application include, e.g. cryogenic protectors such as mannitol, sucrose, lactose, glucose, or glycine (to protect the protein from degradation during lyophilization), antimicrobial preservatives such as methyl and propyl parabens and benzyl alcohol; antioxidants such as EDTA, citrate and BHT (butylated hydroxytoluene); and surfactants such as poly(sorbates) and poly(oxyethylenes).

The identification of patients needing treatment for various conditions including osteoporotic or osteopenic conditions may be accomplished by procedures which are well known in the art. These procedures include measurement of bone mass/density using dual-energy X-ray absorptiometry (DEXA), Kilgus et al., *J. Bone & Joint Surgery*, 75–B: 279–287 (1992); Markel et al., *Acta Orthop Scand*, 61:487–498 (1990); and quantitative computed tomography (QCT), Laval-Jeantet et al., *J Comput Assist Tomogr*, 17:915–921 (1993); Markel, *Calcif Tissue Int*, 49:427–432 (1991); single-photon absorptiometry, Markel et al. *Calcif Tissue Int*, 48:392–399 (1991); ultrasound transmission velocity (UTV); Heaney et al., *JAMA*, 261:2986–2990 (1989); Langton et al., *Clin Phys Physiol Meas*, 11:243–249 (1990); and radiographic assessment, Gluer et al., *J Bone & Mineral Res*, 9:671–677 (1994). Other methods of identification of patients at risk of bone fracture include assessment of age-related factors, such as cognisance, as well as prior occurrence of osteoporosis-related fractures. Porter et al., *BMJ*, 301: 638–641 (1990); Hui et al., *J Clin Invest*, 81:1804–1809 (1988). The above publications are hereby incorporated by reference herein.

The dosage regimen will be determined by the attending physician considering various factors which modify the action of the composition, e.g., amount of tissue desired to be formed, the site of tissue damage, the condition of the damaged tissue, the size of a wound, type of damaged tissue, the patient's age, sex, and diet, the severity of any infection, time of administration and other clinical factors. The dosage may vary with the type of vehicle carrier or matrix used in the reconstitution and the types of additional proteins or DNA sequences in the composition. The addition of other known growth factors to the final composition, may also affect the dosage.

The preparation and formulation of such physiologically acceptable nucleic or protein compositions, having due regard to pH, isotonicity, stability and the like, is within the skill of the art. The therapeutic compositions are also presently valuable for veterinary applications due to the lack of species specificity in TGF-β proteins. Particularly domestic animals and thoroughbred horses in addition to humans are desired patients for such treatment with the compositions of the present invention.

Progress can be monitored by periodic assessment of tissue formation growth and/or repair. The progress can be monitored by methods known in the art, for example, X-rays, arthroscopy, histomorphometric determinations and tetracycline labeling and various methods set forth in the examples below.

The invention, in certain of its embodiments, is illustrated by the examples below. These examples are not limiting. As will be appreciated by those skilled in the art, many variations and combinations of the following examples are available. These combinations and variations constitute a part of the present invention.

EXAMPLE I

Systemic Administration of BMP-6

A. BMP-6 Adenoviral Vectors

The full length BMP-6 clone defines a 1539 base-pair open reading frame that encodes the 513-amino acid hBMP-6. The human BMP-6 cDNA was isolated as a SalI fragment from the BMP-6EMC vector, and the ends were filled in with Vent Polymerase (New England Biolabs, Beverly, Mass.). The Adori 1-1 BMP-6 vector was created with the insertion of the BMP-6 cDNA into the EcoRV restriction site of the adenovirus vector Adori 1-1. The final construct was verified by extensive restriction mapping and full-length sequencing of the BMP-6 insert. The Adori 1-1 EGFP (enhanced green fluorescence protein) vector was derived from a digest of pEGFP-N1 (CLONTECH Laboratories, Inc., Palo Alto, Calif.) with EcoR1 and Not1 and the EGFP cDNA was inserted between the EcoR1 and Not1 sites of Adori 1-1. The Adori 1-1 EGFP construct was confirmed by restriction mapping and 5'-end sequencing. Expression of hBMP-6 and GFP mRNA transcripts is driven from the cytomegalovirus (CMV) immediate early promoter and enhancer sequence. The expression cassette is located downstream of the SV40 origin and enhancer, and 0–1 map units of the adenovirus type 5(Ad5). The SV40 splice donor and acceptor sequence is located between the CMV promoter and the cDNA. Following the insert is a SV40 poly A site, 9–16 map units of Ad5, and the puc 19 origin.

Replication-defective, E1 and E3 minus, type 5 (del327) recombinant adenovirus was generated by homologous recombination in human embryonic kidney 293 cells (ATCC, Rockville, Md.). Virus was generated by cotransfection of Adori expression plasmids, described above, and 9 to 36 map units of adenovirus backbone. Recombinant adenovirus was amplified and released from 293 cells by three cycles of freeze thawing. The virus was further purified by centrifugation through two cesium chloride gradients and dialyzed to equilibrium against phosphate buffered saline, pH 7.2 at 4oC. Following dialysis, glycerol was added to a final concentration of 10% and the virus was stored at −80oC until use. Virus concentration, expressed in particles/ml, was determined by measuring the optical density at 260 nm. Endotoxin levels were measured with the use of a Limulus Amebocyte Lysate kit (BioWhittaker, Walkersville, Md.). The virus was further characterized by PCR amplification of the insert using vector specific primers:

```
                                               (SEQ ID NO:1)
    Forward Primer: 5'-TGGATGTTGCCTTTACTTCTA-3'

(SEQ ID NO: 2)
    Reverse Primer: 5'-TTCACTGCATTCTAGTTGTG-3'
``` or BMP-6 specific primers:

```
                                               (SEQ ID NO:3)
    Forward Primer: 5'-TGTGAACCTGGTGGAGTACG-3'

(SEQ ID NO:4)
    Reverse Primer: 5'-AAGAACCGAGATGGCATTTAGC-3'
```

PCR products were sequenced to confirm the integrity of the insert. Expression of the transgene and secretion of mature BMP-6 were confirmed by metabolic labeling of 293 cells and immunoprecipitation with a BMP-6 selective monoclonal antibody.

B. Closed-Femur Fracture Model

C57BL/6 male mice (Jackson Lab.) between the ages of 12 and 16 weeks were anesthetized with Pentobarbital (60 mg/kg, IP). A sterile ocular ointment was applied to both eyes for protection. The upper-right hind limb was shaved down to the skin and the exposed skin was scrubbed sequentially with an ethanol and Duraprep pads.

After surgical preparations, mice were placed in a sterile surgical field. A 5–10 mm incision was created dorsal to the femoral head. A 25 gauge, 1 inch needle was inserted through the trochanteric fossa and pushed down the marrow canal to the distal femur. After needle insertion, the needle was cut just below the skin. The incision was closed with the use of Nexaband surgical glue. Mice were monitored during the surgical procedure to maintain anesthesia and body temperature.

Closed femur fractures were created in a manner similar to that described by Bonnarens and Einhorn (J. Orthop. Res. 2:97–101, 1984.). The fracture apparatus is shown in FIG. 1.

The pre-pinned, right leg of a mouse was securely positioned such that the middle of the femur rested between the two-pronged animal support stage and the blunt blade. A 150 gram weight was raised to a height of 7.5 cm and then dropped onto the spring below. The fracture apparatus was adjusted so that the impact displacement of the blunt blade towards the femur was about 1 mm.

Each mouse was removed from the fracture apparatus after a single impact trauma and subjected to radiographic analysis with the use of a digital camera x-ray cabinet (Faxitron X-Ray Corporation; MX-20). Animals were radiographed to assess both the placement of the intramedullary pin and the quality of the fracture. Pin placement was judged successful if: I) surgical insertion did not exceed five minutes per mouse or necessitate excessive animal manipulation; ii) pin was placed in middle of medullary canal; and iii) pin was not bent or sticking into another part of the femur. Fractures were judged successful if: I) fracture occured mid-femur; ii) fracture was transverse and not comminuted. Animals that did not meet these criteria were euthanized immediately.

Mice which met the radiographic criteria were allowed to recover on a warming blanket, while being monitored.

C. Effect of Adenoviral Constructs on Fracture Repair

Mice with femur fractures were randomly assigned to two groups before they recovered from surgical anesthesia. Mice in group 1 received a 50 ul injection of adenovirus-GFP in the tail vein. Mice in group 2 received a 50 ul injection of adenovirus-BMP-6 in the tail vein. The number of viral particles administered to each animal was $5 \times 10^{10}$ particles/injection. Mice were monitored twice a day before scheduled euthanasia on days 5,7 and 10. At the scheduled times, mice were euthanized and subjected to radiographic analysis to assess pin placement and fracture quality. Animals in which the fracture did not appear to be stabilized by the pin were discarded from the study. The right legs of the remaining mice were removed. Intramedullary pins were not removed at this time and the legs (minus the skin and hair) were fixed in a solution of 10% neutral-buffered formalin (Hydrol Chemical Co., Yeadon, Pa.).

D. Histological Analysis of Fractured Femurs

Tissues were sectioned and stained with hematoxylin and eosin.

Day 5

A representative femur from each of the two groups showed the beginnings of a fracture repair process. The repair process was manifested by areas on the section (at 2× magnification) of periosteal cell proliferation adjacent to the fracture. At a higher magnification (20×), areas of active chondrogenesis, as determined by the presence of hypertrophic chondrocytes, were readily apparent in a femur from the BMP-6 group. In contrast, hypertrophic chondrocytes were not readily detected in areas adjacent to the fracture from the GFP group. There were no well defined external calluses at day 5 in either group.

Day 7

There was no well defined external callus around the area of the fracture in a femur from the GFP group. This section appeared similar to the GFP femur from day 5. In contrast, there was an obvious and well-defined external callus around the fractured bone from the BMP-6 group.

Day 10

There was no well defined external callus around the area of the fracture in a femur from the GFP group. At low magnification, this section appeared similar to the GFP-femurs from days 5 and 7. However, at higher magnification, it was possible to see that limited numbers of periosteal cells, adjacent to the fracture, were hypertrophic chondrocytes. In contrast, there was an obvious and well-defined external callus around the fractured bone from the BMP-6 group. This callus had evidence of bone formation and neo-vascularization.

Other areas of bone were damaged during the creation of the fracture. For example, the femoral head was punctured during the process of pin insertion. These additional areas of damaged bone also showed obvious signs of a bone repair/formation process in femurs from the BMP-6 group, but not from the GFP group.

The histological data demonstrates that systemic BMP-6, primarily secreted from hepatocytes, is capable of accelerating fracture repair.

EXAMPLE II

A. Ectopic Formation of Bone

Several independent experiments were performed to assess the osteogenic effects of the hBMP-6 adenoviral vector. In these experiments, female C57Bl/6 SCID or immunocompetent mice were injected intramuscularly, into both quadriceps muscles, with a single dose of adenovirus encoding hBMP-6 or GFP (1 to $2.5 \times 10^{10}$ particles/injection). Mice from each experimental group were sacrificed at various (usually one or two) time points post injection. Tissues were harvested, fixed in formalin, and stained with hematoxylin and eosin for histopathology. In all experiments, hBMP-6 induced endochondral bone formation in muscles derived from immunocompromised and to a lesser extent in immunocompetent mice. The following describes results obtained from an experiment in which immunocompromised mice were used and tissues were collected at five time points post injection.

C57BL/6 SCID female mice (Jackson Lab.) were divided into two groups to study the bone-anabolic effects of hBMP-6. All mice were briefly anaesthetized with the inhalation of isoflurane. Anesthesia was followed by the intramuscular injection of either adenovirus-GFP or adenovirusBBMP-6 into both quadriceps muscles of each mouse. Each quadriceps muscle was injected with $1.25 \times 10^{10}$ virus particles in a volume of 25 microliters. Mice were housed five to a cage on a standard diet of food and water and groups of animals were euthanized on days 2,3,4,7 and 14. Both quadriceps muscles were dissected and removed from the animals and fixed in a solution of 10% neutral-buffered formalin (Hydrol Chemical Co., Yeadon, Pa.). The day 14 mice were subjected to x-ray analysis with the use of a digital camera x-ray cabinet (Faxitron X-Ray Corporation; MX-20). This group of animals was radiographed to assess the formation of ectopic bone in the quadriceps muscles.

Selected muscle samples were set aside and total RNA was isolated with the use of the RNAgents and RNeasy kits (Promega and Qiagen, respectively). The RNAgents kit was used as recommended by the manufacturer up to and including RNA precipitation with the use of isopropanol. Isopropanol was washed from the RNA pellet with the use of a 75% ethanol solution. Total RNA was collected with the use of a micro-centrifuge and the pellet was dissolved in lysis buffer from the RNeasy kit. RNA purification was performed as recommended by the manufacturer. Total RNA was eluted in water and the concentration determined with the use of a spectrophotometer.

The RT-PCR was used to measure relative levels of GFP and BMP-6. RT-PCR was performed with the use of an ABI PRISM 7700 Sequence Detection System (Applied Biosystems). Primers and probes relied upon a nucleotide sequence, located within the SV40 poly A sequence, common to both GFP and BMP-6 adenoviral constructs. The primers and probes used were as follows:

```
Forward Primer:                      (SEQ ID NO: 5)
5'-GACATGATAAGATACATTGATGAGTTTGG-3'

Reverse Primer:                      (SEQ ID NO: 6)
5'-GCAATAGCATCACAAATTTCACAAAT-3'

Taqman Probe:                        (SEQ ID NO: 7)
5'-CAAACCACAACTAGAATGCAGTGAAAAAAATGCTT-3'
```

Before the RT-PCR was performed, all total RNA samples were subjected to treatment with RNase-free DNase to remove trace amounts of genomic DNA. The Taqman EZ RT-PCR CORE REAGENTS kit (Perkin Elmer) was used in accordance with the manufacturer's instructions. The PCR took place in 50 ul solutions that contained 50 ng of total RNA and 5 uM of probe and primers. The PCR conditions were as follows:

| | | |
|---|---|---|
| Stage 1: | 50° C. for 2 min. | |
| | 60° C. for 30 min. | |
| Stage 2: | 95° C. for 5 min. | |
| Stage 3: | 95° C. for 15 sec. | X40 |
| | 60° C. for 1 min. | |

This analysis demonstrated the local expression of mRNA for GFP and BMP-6 in quadriceps muscles.

D. Histological Analysis of Quadriceps Muscles

Tissues were sectioned and stained with hematoxylin and eosin.

Injection of adenovirus-GFP did not lead to the formation of ectopic bone in muscle as assessed by visual inspection of the muscle, x-ray radiographs and histology. Histological analysis of the tissue sections revealed acute and subacute inflammation which was characterized by neutrophil, lymphocyte and macrophage infiltration. This cellular infiltration was detected as early as day 2, appeared to peak on days 4 and 7 and appeared to be resolved on day 14. In addition to cellular infiltration, there was also evidence of edema and skeletal muscle fiber degeneration on days 3 and 4 and muscle fiber regeneration on days 7 and 14.

Injection of adenovirus-BMP-6 did lead to the formation of ectopic bone in muscle as assessed by visual inspection of the muscle, x-ray radiographs and histology. It was possible to detect an increase in the size of the muscle as early as day 4 after the injection. X-ray images showed the presence of radio-opaque masses in the muscles of the day 14 animals. Histological analysis of the tissue sections revealed acute inflammation on days 2 and 3. Mesenchymal cell proliferation was observed on days 4, 7 and 14. Cartilaginous tissue was evident on days 7 and 14 and marked bone formation was clearly identified on day 14.

These data demonstrate that intramuscular administration of adenovirus-BMP-6 results in endochondral bone formation.

EXAMPLE III

Adenovirus/BMP-6 Accelerates Osteotomy Healing in a Rabbit Ulna Model

The rabbit ulna model was used to determine if percutaneous injection of adenovirus containing BMP-6 cDNA could be used to accelerate osteotomy healing. This model has been used as a screening model to demonstrate acceleration of osteotomy healing in response to surgical implantation of the rhBMP-2 on a collagen sponge and in a calcium phosphate carrier.

A. Methods

Bilateral mid-diaphyseal ulna 1–2 mm osteotomies were created in 18 adult male rabbits. One following surgery, 200 ml containing $1\times10^{12}$ adenovirus/BMP-6 particles was injected percutaneously into an osteotomy in 12 animals. A similar volume containing the same number of adenovirus/GFP particles was injected into an osteotomy in the remaining 6 animals. The adenovirus/GFP animals served as controls for the effect of administering adenovirus without BMP-6 cDNA. In both groups the contralateral osteotomy served as an untreated surgical control. Intra-muscular injections of adenovirus/GFP were also administered in a number of the animals to validate the efficacy of the viral vector system to express the delivered cDNA. Six of the animals in the adenovirus/BMP-6 group were euthanized at 6 weeks and 8 weeks after surgery. The animals in the adenovirus/GFP adenovirus/GFP group were euthanized 6 weeks after surgery. Outcome measures included serial radiography, torsional biomechanics, histology and GFP expression.

B. Results

Histologic evaluation of the intramuscular adenovirus/GFP injections verified that there was cDNA expression following viral injection. Serial radiographs revealed the presence of mineralized callus as early as two weeks after injection of the adenovirus/BMP-6 (3 weeks after creating the osteotomy). At 6 weeks after creating the osteotomy there was bridging mineralized callus across the osteotomy site in all of the adenvirus/BMP-6 injected animals. The osteotomy was bridged and the osteotomy was no longer visible in the adenovirus/BMP-6 limbs at 8 weeks after creating the osteotomy. The appearance of mineralized bone and bridging callus was delayed in the surgical control osteotomies and the osteotomies injected with adenovirus/GFP. All of the surgical control and adenvirus/GFP injected limbs had visable osteotomy lines at 8 weeks.

Maximum torsional strength and stiffness osteotomies were greater in the adenovirus/BMP-6 limbs compared to the contralateral surgical control limbs at both 6 and 8 weeks after creating the osteotomy (Table 1 and 2). Maximum torsional strength and stiffness in the adenvirus/BMP-6 osteotomies were equivalent to normal rabbit ulnas at both these time points. Maximum torsional strength for the contralateral surgical controls was 44% and 66% of value for normal rabbit ulnas at 6 and 8 weeks after creating the osteotomy. Torsional stiffness was 56% and 72% of the value for normal rabbit ulnas at 6 and 8 weeks after creating the osteotomy. Torsional strength and stiffness were similar in the adenovirus/GFP limbs compared to the contralateral surgical controls at 6 weeks after creating the osteotomy.

The results of this study indicate that percutaneous injection of adenovirus/BMP-6 administered one week after surgery accelerates osteotomy healing in the rabbit ulna model. There was no effect of administering the adenovirus without BMP-6. The use of adenovirus containing cDNA for BMP-6 represents a potential injectable treatment for accelerating closed fracture repair in humans.

TABLE 1

Torsional Strength (Nm: Mean ± SD)

| Time | AdenoBMP-6 | Surgical CT | AdenoGFP | Surgical CT | Normal |
|---|---|---|---|---|---|
| 6 weeks | 0.63 ± 0.21 | 0.29 ± 0.26 | 0.32 ± 0.23 | 0.29 ± 0.18 | 0.66 ± 0.15 |
| 8 weeks | 0.67 ± 0.20 | 0.43 ± 0.17 | | | 0.66 ± 0.15 |

TABLE 2

Torsional Stiffness (Nm/deg: Mean ± SD)

| Time | AdenoBMP-6 | Surgical CT | AdenoGFP | Surgical CT | Normal |
|---|---|---|---|---|---|
| 6 weeks | 0.036 ± 0.015 | 0.018 ± 0.017 | 0.017 ± 0.014 | 0.016 ± 0.012 | 0.032 ± 0.008 |
| 8 weeks | 0.038 ± 0.016 | 0.023 ± 0.012 | | | 0.032 ± 0.008 |

The foregoing descriptions detail presently preferred embodiments of the present invention. Numerous modifications and variations in practice thereof are expected to occur to those skilled in the art upon consideration of these descriptions. Those modifications and variations are believed to be encompassed within the claims appended hereto.

What is claimed is:

1. A method for promoting osteogenesis in a patient comprising systemic administration of an effective amount of a composition comprising a replication-defective adenovirus comprising a CMV promoter, wherein the promoter is operatively linked to a DNA sequence encoding a bone morphogenetic protein (BMP), wherein the DNA sequence is contained within a replication-defective, E1 and E3 minus, type 5 (del327) recombinant adenovirus, and wherein the tropism of the adenovirus is not modified.

2. A method for promoting fracture repair in a patient comprising systemic administration of an effective amount of a composition comprising a replication-defective adenovirus comprising a CMV promoter, wherein the promoter is operatively linked to a DNA sequence encoding a bone morphogenetic protein (BMP), wherein the DNA sequence is contained within a replication-defective, E1 and E3 minus, type 5 (del327) recombinant adenovirus, and wherein the tropism of the adenovirus is not modified.

3. The method of claim 1 or claim 2, wherein the bone morphogenetic protein is selected from the group consisting of BMP-2, BMP-4, BMP-5, BMP-6, BMP-7, BMP-10, BMP-12, BMP-13, BMP-15, BMP-16, and MP52.

4. The method of claim 3, wherein the bone morphogenetic protein is BMP-6.

* * * * *